United States Patent
Njoroge et al.

(10) Patent No.: US 9,624,487 B2
(45) Date of Patent: Apr. 18, 2017

(54) METHODS AND APPARATUSES FOR NUCLEIC ACID PURIFICATION

(71) Applicant: California Institute of Technology, Pasadena, CA (US)

(72) Inventors: Samuel Njoroge, Pasadena, CA (US); George Maltezos, Fort Salonga, NY (US); Axel Scherer, Barnard, VT (US); John B. Gorman, Carlsbad, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/069,697

(22) Filed: Nov. 1, 2013

(65) Prior Publication Data

US 2014/0134078 A1   May 15, 2014

Related U.S. Application Data

(60) Provisional application No. 61/721,878, filed on Nov. 2, 2012.

(51) Int. Cl.
    *C12N 15/10*    (2006.01)
    *B01D 15/22*    (2006.01)

(52) U.S. Cl.
    CPC .......... *C12N 15/101* (2013.01); *B01D 15/22* (2013.01)

(58) Field of Classification Search
    CPC .............................. C12N 15/101; B01D 15/22
    See application file for complete search history.

(56) References Cited

U.S. PATENT DOCUMENTS

| 8,222,023 B2 | 7/2012 | Battrell et al. |
| 2002/0039783 A1* | 4/2002 | McMillan et al. ......... 435/287.2 |
| 2002/0187074 A1* | 12/2002 | O'Connor ............ B01F 5/0682 422/82.05 |

(Continued)

FOREIGN PATENT DOCUMENTS

EP        2007905        8/2012

OTHER PUBLICATIONS

Bogdanov, E. et al., "Silicon Dioxide Thin Film Mediated Single Cell Nucleic Acid Isolation," Plos One, 2013, Vo. 8, Issue 7, e68280, pp. 1-6.

(Continued)

*Primary Examiner* — Lore Jarrett
(74) *Attorney, Agent, or Firm* — Knobbe, Martens, Olson & Bear, LLP

(57) ABSTRACT

An apparatus for purifying nucleic acid can include a disposable cartridge having a layered configuration, and a disposable syringe for coupling to the disposable cartridge such that a fluid can be delivered to or withdrawn fluid from the disposable cartridge using the syringe. At least one layer of the disposable cartridge can include a cut-out for forming a functional unit of the disposable cartridge, and at least one layer of the disposable cartridge can be joined to an adjacent layer of the disposable cartridge by an adhesive material layer. The functional unit can include a fluid channel between an access port on the first surface of the disposable cartridge and the fluid pouch. The apparatus can include a disposable silica-containing material for binding with the nucleic acid. The apparatus can include a heating element and a temperature sensor for heating the disposable silica-containing material.

21 Claims, 32 Drawing Sheets

(56) References Cited

U.S. PATENT DOCUMENTS

| | | | |
|---|---|---|---|
| 2004/0072375 A1* | 4/2004 | Gjerde | B01J 20/285 436/541 |
| 2008/0087554 A1* | 4/2008 | Norris et al. | 205/792 |
| 2009/0148933 A1* | 6/2009 | Battrell et al. | 435/287.2 |
| 2010/0047914 A1* | 2/2010 | Peyman et al. | 436/86 |
| 2012/0171759 A1 | 7/2012 | Williams et al. | |

OTHER PUBLICATIONS

Bordelon, H et al., "A Magnetic Bead-Based Method for Concentrating DNA from Human Urine for Downstream Detection," Plos One, vol. 8, Issue 7, e68369, pp. 1-9, Jul. 2013.

Dharmasiri, U. et al., "High-Throughput Selection, Enumeration, Electrokinetic Manipulation, and Molecular Profiling of Low-Abundance Circulating Tumor Cells Using a Microfluidic System," Anal. Chem., vol. 83, Issue 6, 2011, pp. 2301-2309.

Kapustin, D. V. et al., "Novel Composite Matrices Modified With Nanolayers of Polymers as Perspective Materials for Separation of Biomolecules and Bioanalysis," Nanomedicine, vol. 6, Issue 2, 2011, pp. 241-255.

Liu, C. et al., "Membrane-Based, Sedimentation-Assisted Plasma Separator for Point-of-Care Applications," Anal. Chem., vol. 85, Issue 21, 2013, pp. 10463-10470.

Njoroge, S. K. et al., "Integrated Continuous Flow Polymerase Chain Reaction and Micro-capillary Electrophoresis System With Bioaffinity Preconcentration," Electrophoresis, vol. 32, Issue 22, 2011, pp. 3221-3232.

Rittich, B. et al., "SPE and Purification of DNA Using Magnetic Particles," J. of Sep. Sci. 2013, vol. 36, Issue 15, pp. 2472-2485.

Strotman, L. et al., "Selective Nucleic Acid Removal via Exclusion (SNARE): Capturing mRNA and DNA from a Single Sample" Anal. Chem., vol. 85, Issue 20, 2013, pp. 9764-9770.

Thomas, P. C. et al., "Nucleic Acid Sample Preparation Using Spontaneous Biphasic Plug Flow," Anal. Chem., vol. 85, 2013, pp. 8641-8646.

Wang, J. et al., "Microfluidic Platform for Isolating Nucleic Acid Targets Using Sequence Specific Hybridization," Biomicrofluidics 7 044107, 2013, pp. 1-12.

Wang, S. et al., "Two-dimensional Nitrosylated Protein Fingerprinting by Using Poly (methyl methacrylate) Microchips," Lab Chip, vol. 12, Issue 18, 2012, pp. 3362-3369.

International Search Report and Written Opinion from co-pending PCT International Application No. PCT/US2013/068015, mailed Mar. 6, 2014 in 7 pages.

\* cited by examiner

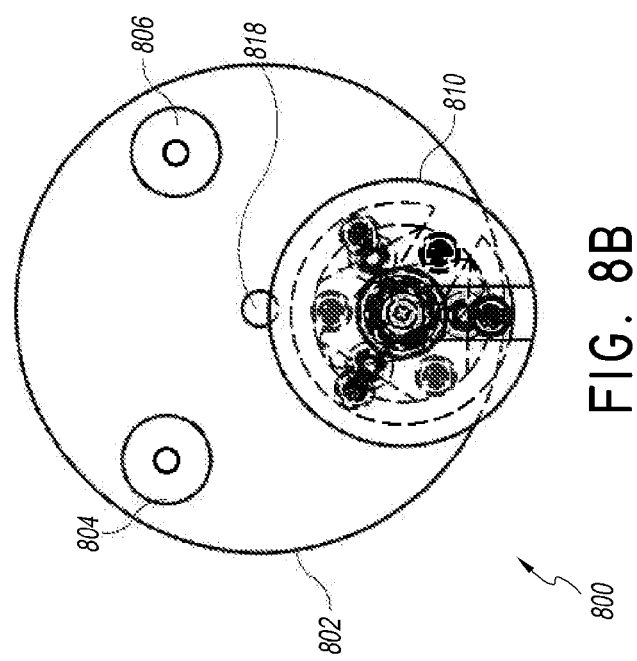
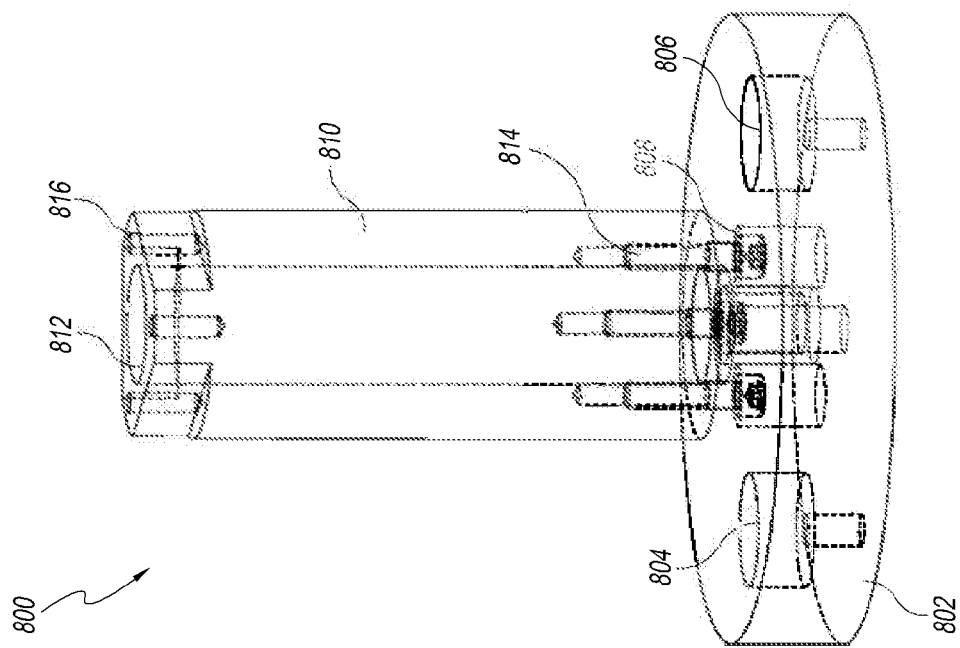

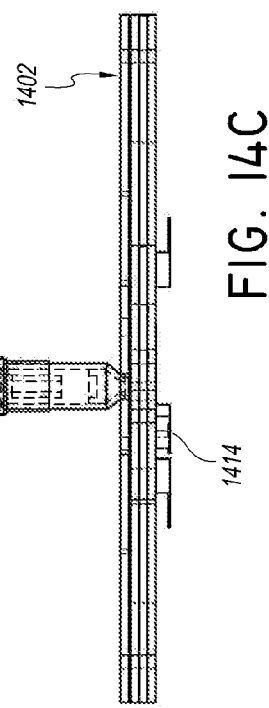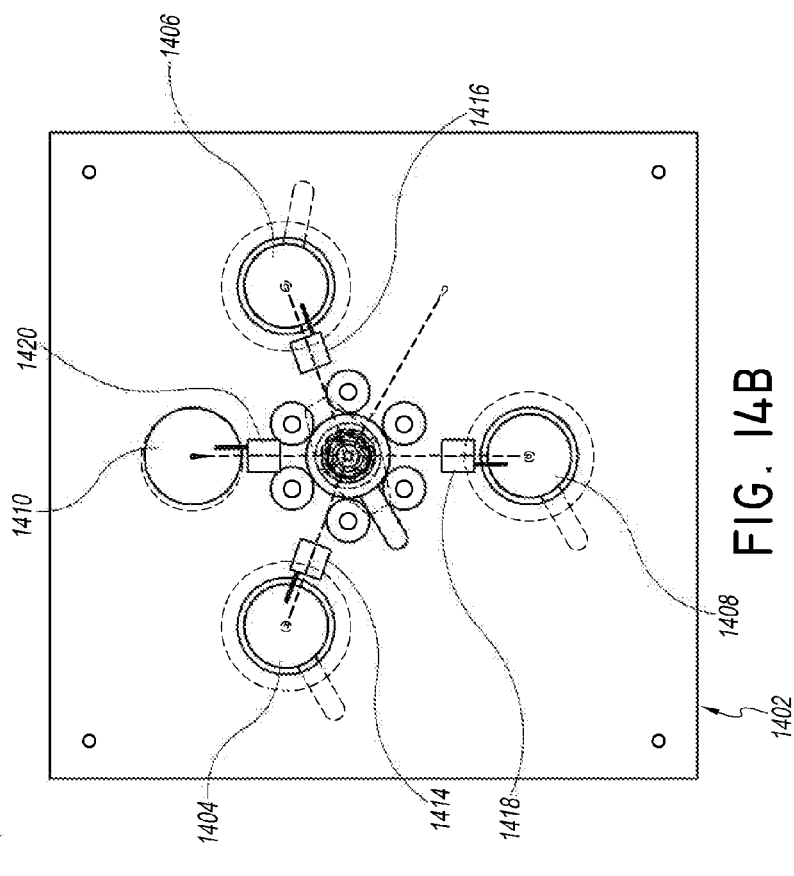
FIG. 14C
FIG. 14B

METHODS AND APPARATUSES FOR NUCLEIC ACID PURIFICATION

CROSS REFERENCE TO RELATED APPLICATIONS

This application claims priority benefit of U.S. Provisional Patent Application Ser. No. 61/721,878, filed Nov. 2, 2012, entitled "SILICA BASED NUCLEIC ACID PURIFICATION AUTOMATED DISPOSABLE," which is incorporated herein by reference in its entirety.

BACKGROUND

Field

The present disclosure relates generally to methods and apparatuses for purification of nucleic acid.

Description of the Related Art

Purification of nucleic acids can be useful for a variety of applications in nucleic acid testing (NAT). Sample preparation including nucleic acid targets (e.g., deoxyribonucleic acid (DNA) and/or ribonucleic acid (RNA)) can be difficult when target molecules are not abundant. Traditional steps of sample preparation may include anticoagulation, filtration, centrifugation, heating, cooling, reagent mixing, extraction, concentration, dilution purification, and/or various other techniques. A sample preparation process can be time consuming, involve intensive manual operations, and/or utilization of numerous instruments.

Additionally, nucleic acid testing (NAT) can involve use of reduced sample sizes, further complicating traditional processes used in purification of nucleic acid samples.

SUMMARY

A nucleic acid purification kit can include a fluid pouch attached to a first surface of a disposable cartridge, the fluid pouch including a first reagent. The kit can include a disposable cartridge having a layered configuration, at least one layer of the disposable cartridge including a cut-out for forming a functional unit of the disposable cartridge, where the at least one layer is joined to an adjacent layer of the disposable cartridge by an adhesive material layer and the functional unit includes a fluid channel between an access port on the first surface of the disposable cartridge and the fluid pouch. In some embodiments, the kit can include a disposable silica-containing compartment for capturing the nucleic acid, where the disposable silica-containing compartment has a distal opening and a proximal opening, the distal opening of the disposable silica-containing compartment being configured to couple to the access port.

In some embodiments, the purification kit can further include a disposable syringe for coupling to the proximal opening of the disposable silica-containing compartment, the disposable syringe being configured to deliver a fluid to or withdraw the fluid from the disposable cartridge. In some embodiments, the functional unit can be an elution fluid chamber configured to retain a fluid for eluting the nucleic acid from the silica-containing compartment.

The disposable cartridge may be valveless. In some embodiments, the disposable cartridge has a valve for controlling fluid transport between the access port and the fluid pouch.

The disposable syringe can include a syringe barrel having an air vent on a sidewall of the syringe barrel, the air vent being configured for drawing air into the syringe. The air vent can include an air filter.

In some embodiments, the silica-containing compartment includes a portion of a sidewall heated by a heater.

In some embodiments, the disposable cartridge can include a plurality of mounting holes on the first surface for coupling with a corresponding plurality of syringe assembly mounting fixtures, the plurality of mounting holes at equal distances from one another surrounding the access port.

An apparatus for purifying nucleic acid can include a disposable cartridge having a layered configuration and including an embedded silica-containing material for capturing the nucleic acid. At least one layer of the disposable cartridge can include a cut-out for forming a functional unit of the disposable cartridge, where the at least one layer is joined to an adjacent layer of the disposable cartridge by an adhesive material layer. The apparatus can include a disposable syringe for coupling to an access port on a first surface of the disposable cartridge, where the disposable syringe is configured to deliver a fluid to or withdraw the fluid from the disposable cartridge such that the silica-containing material is contacted with the fluid.

In some embodiments, the silica-containing compartment is embedded in a sidewall of a first fluid channel within the disposable cartridge, the first fluid channel in fluid being in communication with the access port.

In some embodiments, the apparatus includes a drying chamber in fluid communication with the first fluid channel. In some embodiments, the apparatus includes an elution fluid chamber and a waste fluid chamber in fluid communication with the access port. A sidewall of the drying chamber can include an air vent. In some embodiments, the drying chamber can include an adsorbent material for drying the silica-containing material.

The first fluid channel between the embedded silica-containing material and the drying chamber further can include a wicking material.

In some embodiments, the apparatus includes a first valve for controlling fluid flow to the elution fluid chamber, a second valve for controlling fluid flow to the waste fluid chamber, and a third valve for controlling fluid flow to the drying chamber.

A system for purifying nucleic acid can include a fluid pouch attached to a first surface of a disposable cartridge, the fluid pouch including a first reagent. The system can include a disposable cartridge having a layered configuration, at least one layer of the disposable cartridge including a cut-out for forming a functional unit of the disposable cartridge, where the at least one layer is joined to an adjacent layer of the disposable cartridge by an adhesive material layer The system can include a disposable silica-containing compartment for capturing the nucleic acid, where the disposable silica-containing compartment has a distal opening and a proximal opening, the distal opening of the disposable silica-containing compartment being configured to couple to the access port. In some embodiments, the system includes a disposable syringe for coupling to the proximal opening of the disposable silica-containing compartment, the disposable syringe being configured to deliver a fluid to or withdraw the fluid from the disposable cartridge. The system can include an assembly for holding the disposable syringe at a position relative to the disposable cartridge, the assembly including a syringe holder and a plurality of mounting fixtures for mounting the syringe holder onto the disposable cartridge. The system can include a linear actuator for coupling with a plunger of the syringe configured to apply controlled pressure upon the plunger.

In some embodiments, the system includes an actuator for puncturing the fluid pouch.

In some embodiments, the system includes a resistive heater for heating a portion of a sidewall of the silica-containing compartment.

In some embodiments, the disposable cartridge includes a valve for controlling fluid flow from or into the fluid pouch.

A method for purifying nucleic acid can include loading an analyte sample including the nucleic acid into a disposable silica-containing compartment, where the disposable silica-containing compartment has a distal opening and a proximal opening, the distal opening of the disposable silica-containing compartment being configured to couple to an access port of a disposable cartridge. The method can include applying a suction force using a disposable syringe in fluid communication with the access port to draw a first reagent from a fluid pouch through the access port into the silica-containing compartment for contacting a silica material of the silica-containing compartment with the first reagent, where fluid pouch is attached to a first surface of the disposable cartridge, where the disposable cartridge has a layered configuration such that at least one layer is joined to an adjacent layer of the disposable cartridge by an adhesive material layer, and where at least one layer of the disposable cartridge includes a cut-out for forming a functional unit of the disposable cartridge.

The nucleic acid can include ribonucleic acid (RNA). The nucleic acid can include deoxyribonucleic acid (DNA).

In some embodiments, the method can include drying the silica material subsequent to contacting the silica material with the first reagent, by heating the silica containing compartment.

In some embodiments, the method can include drying the silica material subsequent to contacting the silica material with the first reagent by drawing air into the silica containing compartment through an air vent on a syringe barrel sidewall.

In some embodiments, the functional unit can include an elution fluid chamber. The method can include eluting the nucleic acid from the silica containing compartment by drawing an elution fluid from the elution fluid chamber.

In some embodiments, applying the suction force can include activating a linear actuator coupled to a syringe plunger of the disposable syringe to pull the syringe plunger.

For purposes of summarizing the invention and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

Various features, aspects, and advantages of the present disclosure are described with reference to the drawings of certain embodiments, which are intended to illustrate certain embodiments and not to limit the disclosure. The drawings are not necessarily to scale.

FIGS. 8A through 8D show an example of an assembly for coupling a syringe to a disposable cartridge.

FIGS. 14A through 14C show an example of a purification apparatus which includes a disposable cartridge having a plurality of fluid flow valves.

DETAILED DESCRIPTION

Figure 1A:
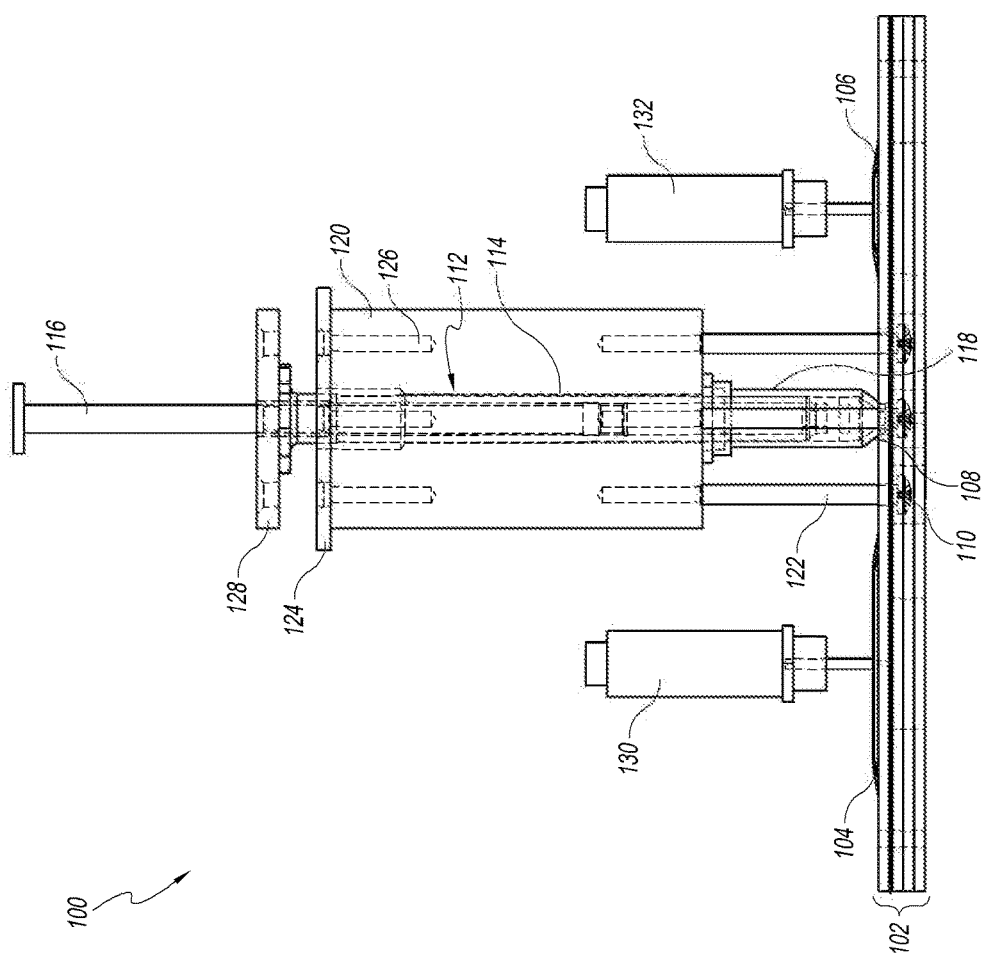
FIGS. 1A and 1B show an example of a purification apparatus.

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

Sample preparation for nucleic acid testing (NAT) can involve purification and isolation of the nucleic acid (NA) from other components (e.g., hemoglobin, lactoferrin, immunoglobin G (IgG), cell debris, heme, amplification inhibitors, ions, excess salts such as KCl and/or NaCl, ionic detergents such as sodium deocycholate, sarkosyl and sodium dodecyl sulfate (SDS), nucleic acid extraction and/or precipitation reagents such as ethanol, isopropanol and phenol, and/or other contaminants). In some embodiments, nucleic acid is purified using one or more chaotropic reagents (e.g., guanidinium hydrochloride and/or guanidinium thiocyanate), where the chaotropic agents are subsequently removed in the purification process. For example, nucleic acid, such as DNA and RNA, may bind to silica containing material in the presence of one or more chaotropic reagents, and may unbind from the silica containing material in the absence of the one or more chaotropic reagents. An analyte solution can include a lysate (e.g., an analyte solution including nucleic acid which had been subjected to a lysis process), which may be contacted with a silica containing material such that the nucleic acid can bind with the silica in the presence of one or more chaotropic agents. The nucleic acid bound to the silica containing material can be washed several times with different wash buffers, and dried (e.g., for removal of organic alcohols such as ethanol and/or isopropanol), before the purified nucleic acid can be eluted. The silica containing material can be desalted with desalting fluid to remove the chaotropic salts, for example for eluting the nucleic acid. The captured nucleic acid can include both DNA and RNA. For example, either the DNA or the RNA may be selectively removed in a downstream process.

In some embodiments, one or more methods and/or apparatuses described herein can facilitate purification of nucleic acid, including purification of reduced quantities of nucleic acid for NAT. In some embodiments, a purification methods and/or apparatuses described herein can be implemented as a standalone process and/or apparatus, and/or can be integrated with other nucleic acid biochemical manipulations processes and/or other downstream processes. For example, one or more components of a purification apparatus can be interfaced with and/or integrated as part of other biochemical manipulations processes, including for example processes for nucleic acid amplification and/or detection.

In some embodiments, a purification apparatus described herein can include one or more disposable components. For example, a purification apparatus can include a cartridge which can be disposable, a portion of the cartridge which can be disposable, a syringe which can be disposable and/or a component of the syringe which can be disposable. In some embodiments, a silica material containing compartment and/or a portion of a silica material containing compartment can be disposable.

A purification apparatus can include a disposable cartridge of various shapes having a layered configuration. For example, the disposable cartridge can be assembled from multiple layers of structural material where the multiple layers can be joined together by adhesive material layers adjacent to each of the multiple structural layers (e.g., assembled using a converter tape technology). A disposable cartridge having such a configuration can facilitate cheap and/or easy to fabricate disposable cartridges (e.g., in comparison to cartridges fabricated using only injection molding). One or more of the layers of a disposable cartridge can have one or more cut-outs (e.g., cut-outs in one or more layers of the structural material and/or the adhesive material layer, can be formed by a laser cutting process, die cutting process, knife cutting process, and/or any other suitable method), the cut-outs having a shape and/or dimension configured to form one or more features of the disposable cartridge. For example, cut-outs in one or more layers of the disposable cartridge can be shaped and/or dimensioned to form one or more fluid chambers, fluid channels, and/or other functional units of the disposable cartridge. For example, adhesive layers (e.g., made of a pressure sensitive adhesive material, for example a silicone pressure sensitive adhesive material) of the disposable cartridge can be patterned to include cut-outs corresponding to one or more features of the disposable cartridge such that the adhesive material does not contact one or more fluids housed within the cartridge. A material and/or a thickness of a layer of disposable cartridge can be selected based on a dimension of a disposable cartridge feature (e.g., a height of a fluid chamber and/or fluid channel which the layer forms a part of) compatibility with an analyte solution and/or a reagent solution, a desired surface roughness, and/or desired mechanical property of the disposable cartridge. The layers of a disposable cartridge can be different from one another, for example a structural material layer can be made of a material different from that of another structural material layer, and an adhesive layer can be made of a material different from another adhesive material layer of the disposable cartridge.

A disposable cartridge can include one or more fluid chambers formed by the plurality of layers and/or have one or more fluid pouches attached to one or more surfaces of the disposable cartridge. In some embodiments, fluid can be released from and/or infused into the one or more fluid pouches and/or chambers by opening one or more air vents (e.g., by puncturing the fluid pouches and/or opening pre-existing air vent). In some embodiments, fluid can be prevent from or substantially prevent from being released from and/or infused into the one or more fluid pouches and/or chambers by closing one or more air vents (e.g., by sealing the fluid pouches and/or sealing a pre-existing air vent). In some embodiments, the disposable cartridge can be a valveless disposable cartridge (e.g., control of fluid flow within the disposable cartridge can be facilitated by opening and/or closing of air vents of fluid chambers and/or pouches). In some embodiments, the disposable cartridge can include one or more valves to facilitate control of fluid flow into, out from and/or within the disposable cartridge.

A purification apparatus can include a device for delivering a fluid into, and/or withdrawing fluid out of one or more chambers of a disposable cartridge of the purification apparatus (e.g., by using a syringe, a pump, and/or any other suitable method). For example, a syringe can be coupled to the disposable cartridge at a desired location, for example at an access opening in the disposable cartridge such that the syringe can be used to provide a positive and/or a negative force for transport of fluid into, out of, and/or within the disposable cartridge. The syringe can be secured to the disposable cartridge using an assembly including various components for mounting the syringe onto the disposable cartridge.

The purification apparatus can include a material for selective binding with an analyte, such as a silica containing material (e.g., a silica based membrane (SBM), such as glass frit) for selective binding with nucleic acid. In some embodiments, a SBM can be integrated in a disposable cartridge (e.g., embedded in a channel within the cartridge). In some embodiments, a disposable cartridge can be coupled to a SBM containing compartment (e.g., a spin column and/or other suitable container). For example, a SBM containing compartment can be coupled to an access opening of a disposable cartridge and placed between a syringe and the disposable cartridge such that one or more fluids contained within the disposable cartridge can be drawn up into the SBM containing compartment using the syringe, including an analyte solution such that the analyte can bind with the SBM and one or more solutions to wash and/or elute analyte bound on the SBM.

FIG. 1A shows a side view of an example of a purification apparatus 100. The purification apparatus 100 can include a disposable cartridge 102, and a syringe 112. For example, the syringe 112 can be coupled to the disposable cartridge 102 at a disposable cartridge access port 108 on a first surface of the disposable cartridge 112. The syringe 112 can be a graduated syringe, for example to facilitate dispensing controlled amounts of fluid. Referring to FIG. 1A, the disposable cartridge 102 can have a layered configuration. For example, the disposable cartridge 102 can be fabricated from a plurality of sheets having various openings cut into the sheets for forming channels, chambers, and/or other openings within the disposable cartridge 102, the plurality of sheets assembled into the cartridge using adhesive layers between adjacent sheets. In some embodiments, the disposable cartridge 102 can be fabricated using a converter tape process.

As shown in FIG. 1A, in some embodiments, the disposable cartridge 102 can include a first fluid pouch 104 and a second fluid pouch 106. The first fluid pouch 104 can be configured to contain a first reagent solution and the second fluid pouch 106 can be configured to contain a second reagent solution (e.g., the first fluid pouch 104 and the second fluid pouch 106 can include a premeasured quantity of the first reagent solution and a premeasured quantity of the second reagent solution, respectively). The first fluid pouch 104 and the second fluid pouch 106 may be attached to a first surface of a layer of the disposable cartridge 102, such as by using an adhesive material (e.g., a pressure sensitive adhesive material). Other suitable mechanical means for coupling the first fluid pouch 104 and the second fluid pouch 106 to the adjacent layer of the disposable cartridge 102 may also be suitable.

In some embodiments, the first fluid pouch 104 and/or the second fluid pouch 106 can be punctured by one or more actuators to facilitate delivery of and/or withdrawal of reagent solutions form the fluid pouches, for example for delivery of the reagent solutions to the silica based membrane. The first fluid pouch 104 may be punctured by a first actuator 130, and the second fluid pouch 106 may be punctured a second actuator 132. For example, the syringe 112 can apply a suction force prior to, during, and/or after a fluid pouch is punctured by an actuator, facilitating delivery of the reagent solution from the fluid pouch to a silica based membrane.

The syringe 112 can include a barrel 114 and a plunger 116, the plunger 116 movable within the barrel 114 in a distal and/or a proximal direction. In some embodiments, a distal end of the syringe 112 can be coupled to a compartment 118 having a silica based membrane (SBM) for capturing nucleic acid. In some embodiments, a compartment 118 (e.g., a spin column) including a silica based membrane (SBM) can be in fluid communication with a distal orifice of the syringe 112. For example, the SBM containing compartment 118 can be between the syringe 112 and the disposable cartridge 102, where an opening at a proximal end the SBM containing compartment 118 can be coupled to the syringe 112 (e.g., at the distal orifice of the syringe), such that the SBM containing compartment 118 is in fluid communication with the orifice at the distal end of the syringe 112. A distal end of the SBM containing compartment 118 can be coupled to the disposable cartridge 102, for example at an access port 108 on a first surface of the disposable cartridge 102. The SBM containing compartment 118 may have an opening at a distal end coupled to the cartridge such that the SBM containing compartment 118 can be in fluid communication with the access port 108. For example, the opening at the distal end of the SBM containing compartment 118 can be aligned with and coupled to the access port 108 of the disposable cartridge 102 such that reactant solutions and/or analyte containing solutions can be drawn up through the access port 108 from one or more fluid pouches and/or fluid chambers of the disposable cartridge 102 into the SBM containing compartment 108 and over the SBM (e.g., using the syringe 112 to apply positive and/or negative pressure). In some embodiments, the SBM containing compartment 118 can be integrated as part of the syringe.

Figure 1B:
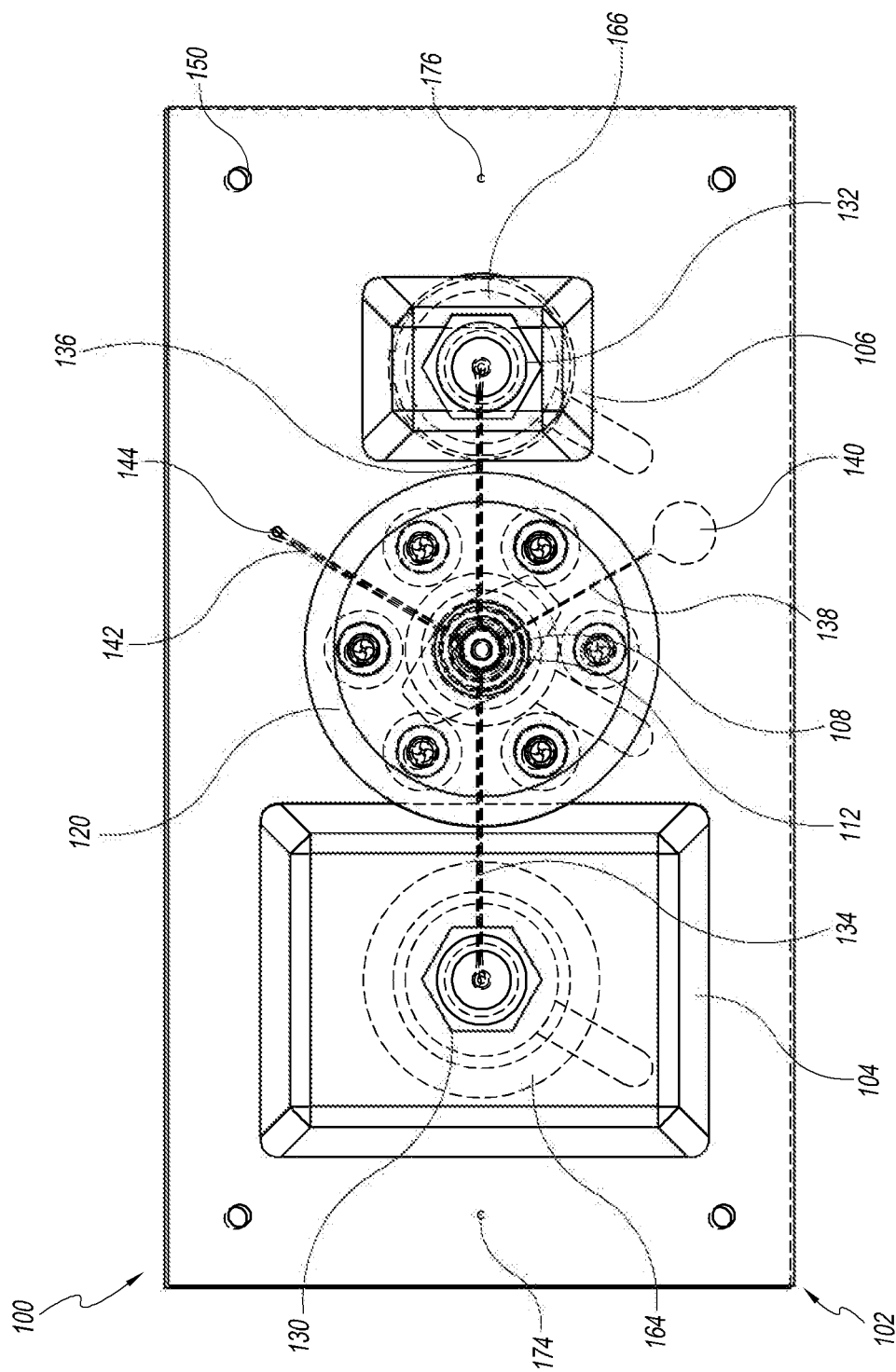

Referring to FIG. 1 A, in some embodiments, a syringe holder 120, one or more mounting fixtures 122, and/or mounting brackets 124, 128, can facilitate positioning of the syringe 112 over the disposable cartridge 102 at a desired location. In some embodiments, the disposable cartridge 102 can include one or more mounting holes 110 for coupling the syringe holder 120 to the disposable cartridge 102. For example, one or more mounting fixtures 122 can be placed into corresponding mounting holes 110 for positioning the syringe holder 120. For example, the one or more mounting fixtures 122 can be one or more mounting screws which can be screwed into one or more corresponding mounting holes 110 in the disposable cartridge 102 for positioning the syringe holder 120 onto the disposable cartridge 102. FIGS. 1A and 1B show a syringe holder 120 coupled to the disposable cartridge 102 using six mounting fixtures 122. More or fewer mounting fixtures 122 may be suitable. An opposite end of the one or more mounting fixtures 122 can be coupled to the syringe holder 120.

FIG. 1B shows a top-down plan view of the purification disposable 100. As described herein, the purification apparatus 100 can include the disposable cartridge 102, and the syringe 112, where a chamber in the syringe 112 formed by the syringe plunger and a sidewall of the syringe barrel is in fluid communication with one or more chambers and/or fluid pouches of the disposable cartridge 102 via the access port 108 of the disposable cartridge 102. For example, the disposable cartridge 102 can include a first fluid channel 134 between the access port 108 and the first fluid pouch 104, a second fluid channel 136 between the access port 108 and the second fluid pouch 106, and/or an elution fluid channel 138 between the access port 108 and the elution fluid chamber 140, such that the first reagent solution, the second reagent solution, and/or the elution fluid can be transported between the access port 108 and the first fluid pouch 104, the second fluid pouch 106 and the elution chamber 140, respectively.

In some embodiments, the disposable cartridge 102 can include a fluid chamber in fluid communication with a corresponding fluid pouch. For example, a fluid chamber can be in fluid communication with a corresponding fluid pouch (e.g., through one or more openings and/or channels between the fluid chamber and the fluid pouch) positioned above the fluid chamber, such as when viewing the disposable cartridge 102 from the first surface of the disposable cartridge 102. Referring to FIG. 1B, a first fluid chamber 164 can be beneath and in fluid communication with the first fluid pouch 104. A second fluid chamber 166 can be beneath and in fluid communication with the second fluid pouch 106. In some embodiments, the first fluid chamber 164 and the second fluid chamber 166 are in fluid communication with the access port 108 (e.g., directly via one or more fluid channels between the fluid chamber and the access port, and/or indirectly via the corresponding fluid pouch). For example, the first fluid channel 134 can be between the first fluid pouch 104 and the first fluid chamber 164 such that the first fluid chamber 164 can be in fluid communication with the access port 108 via the first fluid channel 134. For example, the second fluid channel 136 can be between the second fluid pouch 106 and the second fluid chamber 166 such that the second fluid chamber 166 can be in fluid communication with the access port 108 via the second fluid channel 136.

In some embodiments, the first fluid chamber 164 can be in fluid communication with a first air vent 174. In some embodiments, the second fluid chamber 166 can be in fluid communication with a second air vent 176. An air vent for a fluid chamber can be opened and/or closed to facilitate control of fluid flow into, out from, and/or retention of fluid within the fluid chamber, pressure relief from the fluid chamber, and/or reduce occurrence of hysteresis. For example, the air vent 174 and/or the air vent 176 can be opened to facilitate withdrawal of fluid from and/or infusion of fluid into the first fluid chamber 164 and/or the second fluid chamber 166, respectively. In some embodiments, the air vent 174 and/or the air vent 176 can be closed to facilitate retention of fluid within the first fluid chamber 164 and/or the second fluid chamber 166, respectively, for example after delivery of fluid into the respective chambers (e.g., waste fluid, and/or previously used reagent solutions).

In some embodiments, the first fluid pouch 104 can include a premeasured quantity of a first reagent, the second fluid pouch 106 can include a premeasured quantity of a second reagent, while the first fluid chamber 164 and/or the second fluid chamber 166 can be without or substantially without a fluid. The first reagent and/or the second reagent may then flow into the first fluid chamber 164 and/or the second fluid chamber 166, respectively, once an air vent is created in the first fluid pouch 104 and/or the second fluid pouch 106 (e.g., through puncturing of the respective pouches using an actuator). Subsequently, the first reagent can be drawn from the first fluid pouch 104 and/or the first fluid chamber 164 and the second reagent can be drawn from the second fluid pouch 106 and/or the second fluid chamber 166 (e.g., for delivering the first reagent and/or the second reagent to the silica based membrane (SBM) within the SBM containing compartment 118), such as when a suction force is applied using the syringe 112.

The first fluid chamber 164 and/or the second fluid chamber 166 can provide additional volume within which the first reagent and/or the second reagent may be manipulated, for example when delivering the first reagent and/or the second reagent to the silica based membrane (SBM) containing compartment 118. In some embodiments, additional volume within which to manipulate a reagent solution can reduce creation of back pressure. In some embodiments, the first fluid chamber 164 and/or the second fluid chamber 166 can facilitate storage of used reagent solutions. For example, a first reagent and/or a second reagent previously delivered to the SBM containing compartment 118 for washing the SBM may be returned to the first fluid chamber 164 and/or the second fluid chamber 166 for storage (e.g., reducing a need to extract used reagent solutions from the disposable cartridge 102 while processing an analyte sample, and/or to facilitate storage of reagent solutions in event of mechanical hysteresis).

Nucleic acid bound to the silica based membrane (SBM) can be washed with various wash fluid stored in one or more the fluid pouches of the disposable cartridge 102. For example, washing fluid from respective fluid pouches can be sequentially released and delivered to the SBM using one or more actuators to puncture the fluid pouches (e.g., actuator 130 to puncture fluid pouch 104, actuator 132 to puncture fluid pouch 106) and by applying a suction force using the syringe 112. The syringe 112 can apply a suction force prior to, during, and/or after a fluid pouch is punctured by an actuator, facilitating delivery of the reagent solution from the fluid pouch to the SBM. An actuator can include a variety of suitable devices which include a pointed tip and which can apply a controlled pressure for puncturing a fluid pouch (e.g., including various suitable electro-mechanical actuators).

In some embodiments, a solution containing an analyte (e.g., an analyte solution including the nucleic acid) can be passed through a sample loading port 144 located on the first surface of the cartridge 102, and through a sample input channel 142 to the silica based membrane (SBM) in the SBM containing compartment 118. In some embodiments, a microfluidic connection can be coupled to the disposable cartridge 102 to deliver the analyte solution to the SBM through the sample loading port 144. In some embodiments, a controlled suction force can be applied using the syringe 112 for facilitating delivery of the analyte solution through the sample loading port 144 to the SBM. For example, the plunger 116 of the syringe 112 can be pulled to provide a suction force prior to and/or during passing of the analyte solution through the sample loading port 144, the suction force applied controlled by the level to which the plunger 116 of the syringe 112 is pulled.

Referring to FIG. 1B, in some embodiments, the disposable cartridge 102 can include two or more alignment openings 150, for example to facilitate alignment of the plurality of layers of the cartridge 102. An alignment opening 150 can extend through all of the layers of the disposable cartridge 102. FIG. 1B shows the disposable cartridge 102 including a circular shaped or substantially circular shaped alignment opening 150 in each of the four corners of the disposable cartridge 102 having a rectangular or substantially rectangular shape. More or fewer alignment openings 150 may also be suitable. The alignment openings 150 can have other suitable shapes and/or may be located on different portions of the disposable cartridge 102. For example, a shape, position and/or a number of alignment openings 150 can be selected based on a shape and/or size of the disposable cartridge 102.

In some embodiments, the silica based membrane (SBM) and nucleic acid bound to the SBM can be dried subsequent to being washed, and prior to elution of the nucleic acid. The SBM can be dried with streams of air cycles (e.g., air drawn into the SBM containing compartment 118 from an air vent collocated with the sample loading port 144 and/or an air vent (not shown) on a sidewall of the syringe barrel 114). In some embodiments, the SBM can be dried by heating, for example by resistive heating of the SBM containing compartment 118. In some embodiments, both air drying and heat drying can be utilized.

Figure 2A:
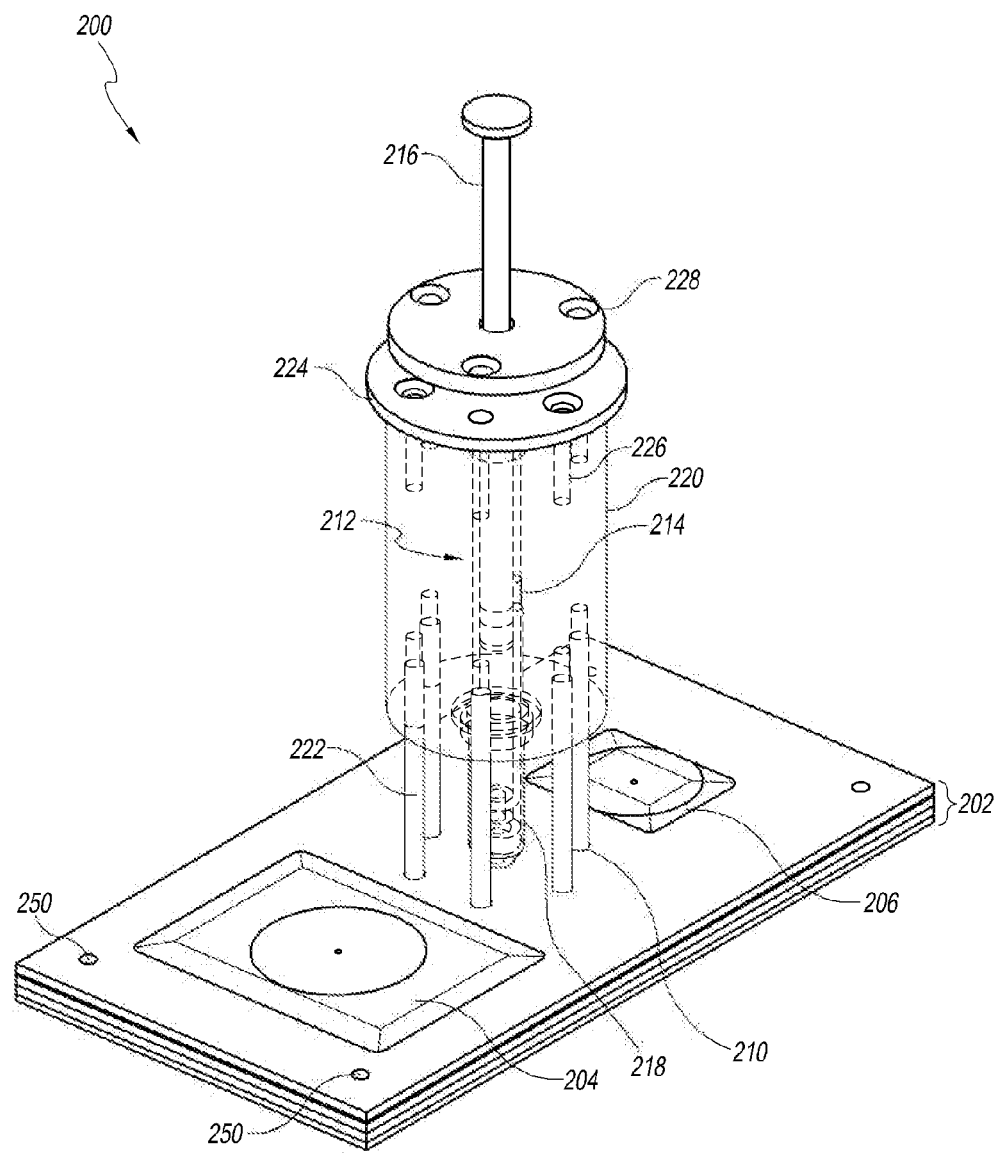
FIGS. 2A and 2B show an example of a purification apparatus.

FIG. 2A shows a perspective view of an example of a purification apparatus 200. The purification apparatus 200 can have a configuration similar to that of the purification apparatus 100 (e.g., as shown in FIGS. 1A and 1B). For example, the purification apparatus 200 can include a disposable cartridge 202 including a first fluid pouch 204 and a second fluid pouch 206 on a first surface of the disposable cartridge 202, the first fluid pouch 204 and the second fluid pouch 206 can be in fluid communication with an access port 260 (shown in FIG. 2B) on the first surface of the disposable cartridge 202. In some embodiments, the apparatus can include a syringe 212 coupled to the disposable cartridge 202. The purification apparatus 200 can include an assembly for placing the syringe 212 at a desired location relative to the disposable cartridge 202, the assembly including a syringe holder 220 coupled to the disposable cartridge 202 by mounting a plurality of mounting fixtures 222 in corresponding mounting holes 210 in the disposable cartridge 202. In some embodiments, the assembly can include a first mounting bracket 224 (e.g., the first mounting bracket can be secured, for example screwed, onto the syringe holder 220 by using a plurality of bracket securing fixtures 226, for example bracket screws), and a second mounting bracket 228 to facilitate holding the syringe 212 in place. An opening at a proximal end of a silica based membrane (SBM) containing compartment 218 can be coupled to an orifice at a distal end of the syringe 212, and an opening at a distal end of the SBM containing compartment can be coupled to the disposable cartridge 202, for example at an access port 260, such that the syringe 212 can be used to apply a suction force (e.g., a negative pressure) and/or an expulsion force (e.g., a positive pressure) upon a first reagent within the first fluid pouch 204 and/or a second reagent within the second fluid pouch 206, when the syringe plunger 216 is moved in a proximal direction within the syringe barrel 214, and when the syringe plunger 216 is moved in a distal direction within the syringe barrel 214, respectively.

Figure 2B:
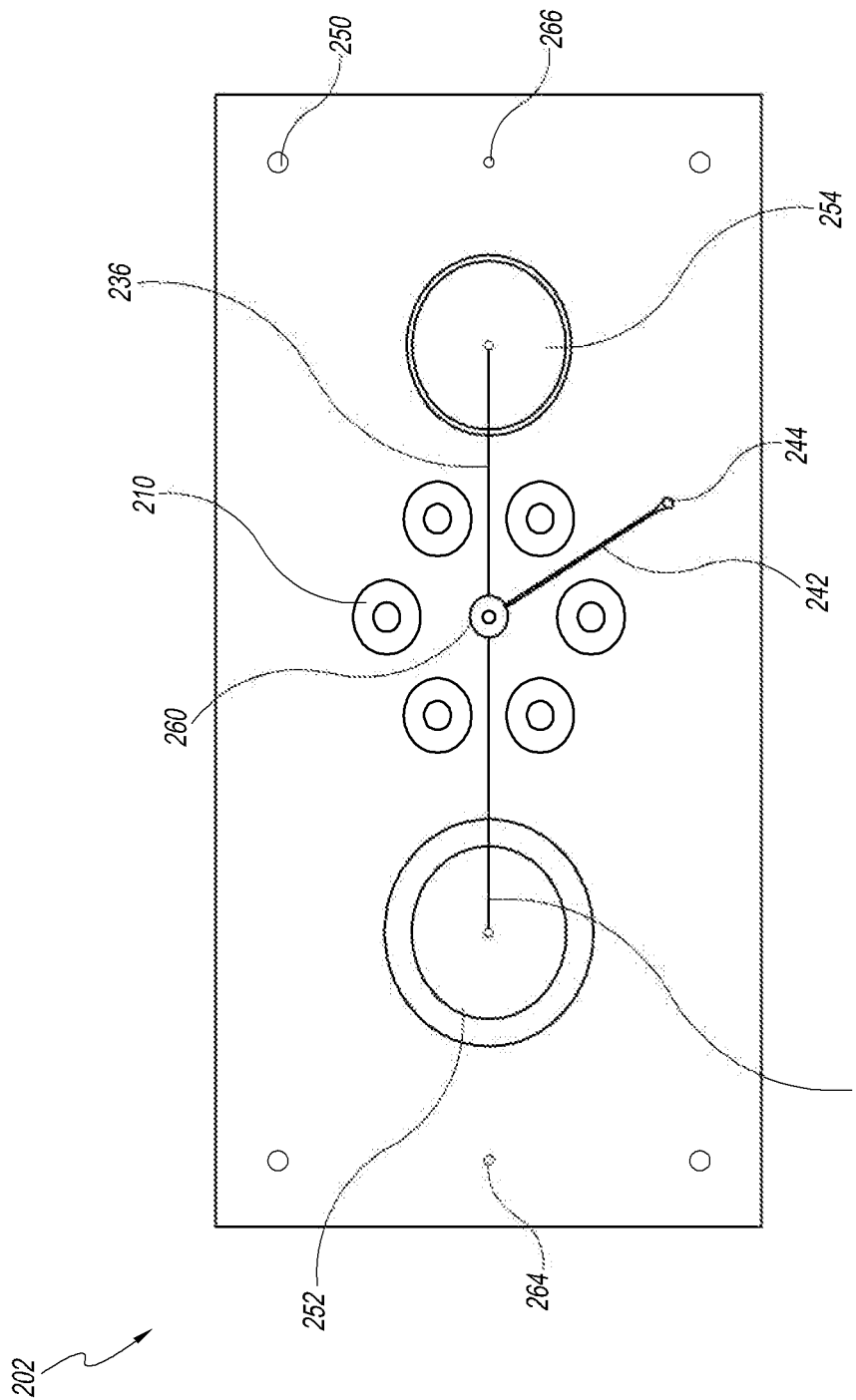

FIG. 2B shows a top-down cross-section view of the disposable cartridge 202. In the top-down cross-section view, an analyte loading port 244 in fluid communication with the access port 260 via an analyte loading channel 242 can be seen. The disposable cartridge 202 can include a first reagent chamber 252 and a second reagent chamber 254, where the first reagent chamber 252 and the second reagent chamber 254 can be in fluid communication with the access port 260 via a first fluid channel 234 and a second fluid channel 236, respectively. For example, the first reagent chamber 252 can be in fluid communication with the first fluid pouch 204 (e.g., the first fluid pouch 204 being positioned above the first reagent chamber 252 such that the first reagent within the first fluid pouch 204 can flow from the first fluid pouch 204 once the first fluid pouch 204 is punctured), and the second reagent chamber 254 can be in fluid communication with the second fluid pouch 206 (e.g., the second fluid pouch 206 being positioned above the second reagent chamber 254 such that the second reagent within the second fluid pouch 206 can flow from the second fluid pouch 206 once the second fluid pouch 206 is punctured). In some embodiments, the first fluid chamber 252 can be in fluid communication with a first air vent 264, and the second fluid chamber 254 can be in fluid communication with a second air vent 266. As described herein, an air vent for a fluid chamber can be opened and/or closed to facilitate control of fluid flow into, out from, and/or retention of fluid within the fluid chamber, pressure relief from the fluid chamber, and/or reduce occurrence of hysteresis.

Referring to FIG. 2B, in the top-down cross-section view, six mounting holes 210 for mounting the assembly which couples the syringe 212 to the disposable cartridge 202, and four alignment holes 250 at each of the four corners of the disposable cartridge 202 can be seen.

The syringe 212 can have various fluid capacities, including for example about 1 milliliters (mL) to about 3 mL. In some embodiments, the syringe 212 can be used to process an analyte solution of about 1 mL (e.g., a solution containing nucleic acid which can be purified using the purification apparatus 200) in less than about 10 minutes, including about 5 minutes, facilitating quick purification of the analyte solution. In some embodiments, the syringe 212 can be used to process an analyte solution of about 3 mL.

Figure 3A:
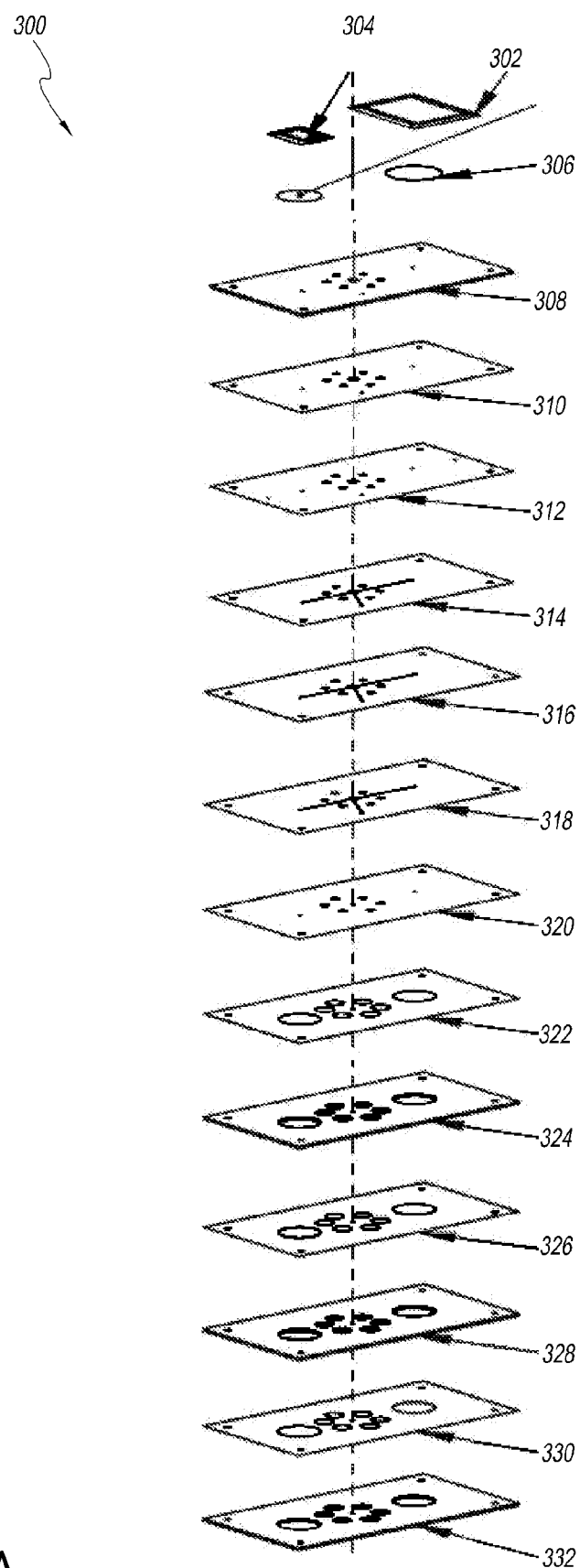
FIGS. 3A and 3B show an example of a disposable cartridge of a purification apparatus.
Figure 3B:
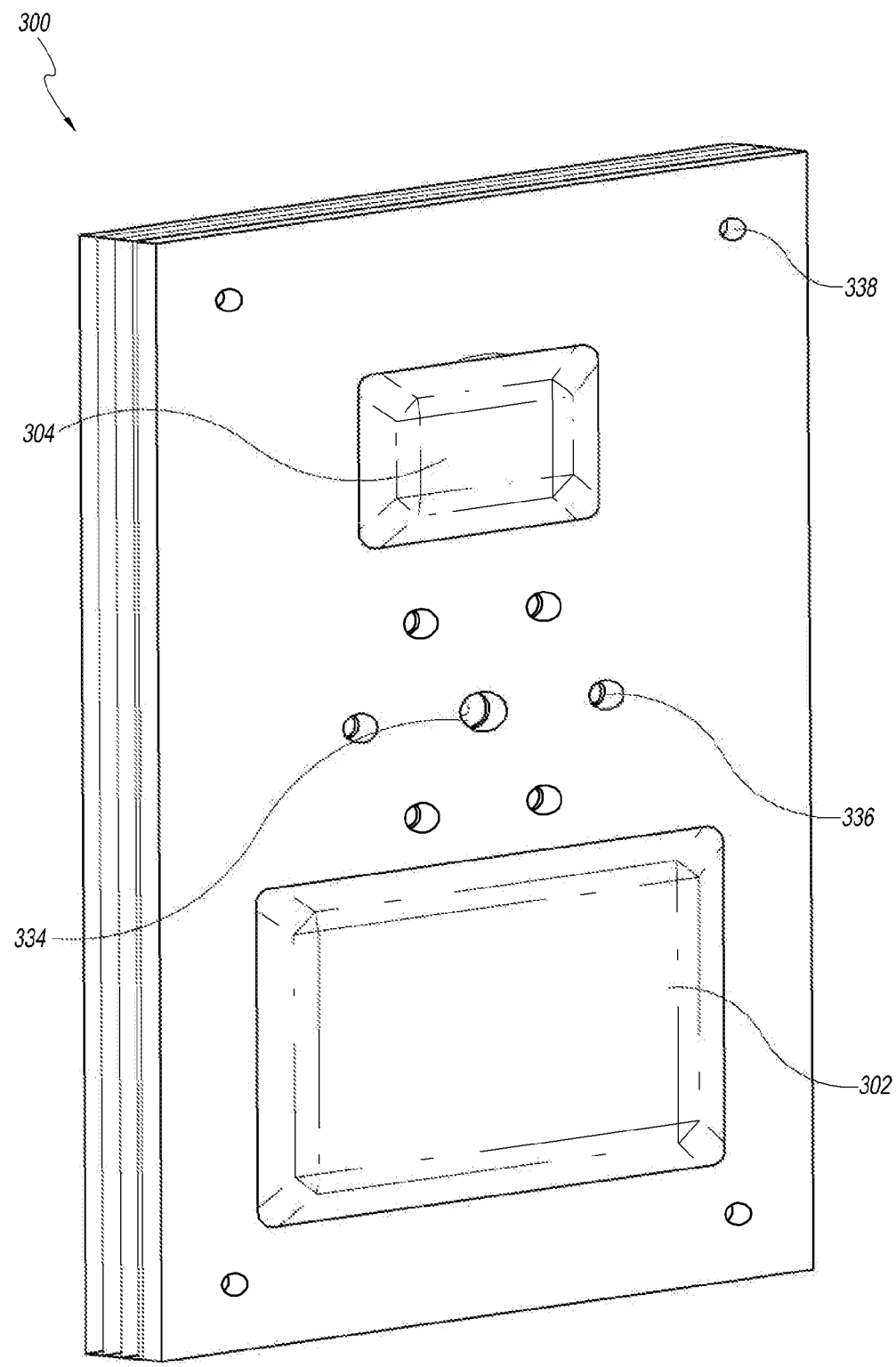

FIG. 3A shows an exploded view of an example of a disposable cartridge 300 having a rectangular or substantially rectangular shape, and FIG. 3B shows a perspective view of the assembled disposable cartridge 300. As described herein, disposable cartridges can have a layered configuration, such that the disposable cartridges can be made from a plurality of layers of materials having cut-outs of various shapes, the plurality of layers being joined together by adhesive material adjacent to each of the plurality of layers (e.g., by using a converter tape process). One or more of the plurality of layers can include one or more cut-outs for forming a feature of the disposable cartridge (e.g., cut-outs having shapes and/or sizes for forming a fluid chamber, a fluid channel, a mounting hole, an access port, and/or an alignment feature having a desired shape and/or size). A thickness of a layer of the disposable cartridge 300 can be selected based on a desired volume of the disposable cartridge feature formed by the layer. FIGS. 3A and 3B shows that the adjacent layers of the disposable cartridge 300 can be adhered to one another to form an assembled disposable cartridge 300 including a first fluid pouch 302 and a second fluid pouch 304 in fluid communication with an access port 334, a plurality of mounting holes 336 (e.g., six mounting holes evenly spaced or substantially evenly spaced around the access port 334) for coupling a syringe assembly to the disposable cartridge 300, and a plurality of alignment holes 338 (e.g., four alignment holes 338 in each of the four corners of the rectangular or substantially rectangular disposable cartridge 300) for facilitating alignment with one another of the plurality of layers of the disposable cartridge 300. In some embodiments, the disposable cartridge 300 can include a first fluid chamber in fluid communication with the first fluid pouch 302 (e.g., the first fluid chamber being defined by one or more layers of the disposable cartridge 300 to which the first fluid pouch 302 is attached) and a second fluid chamber in fluid communication with the first fluid pouch 304 (e.g., the second fluid chamber being defined by one or more layers of the disposable cartridge 300 to which the second fluid pouch 304 is attached).

In some embodiments, the disposable cartridge 300 can include a silica based membrane (SBM), for example the SBM being integrated as part of the disposable cartridge. For example, the SBM can be located near or adjacent to the access port 334 such that an analyte in an analyte solution (e.g., a solution containing a sample of nucleic acid for analysis) can be passed over the SBM and selectively bind to the SBM in the presence of one or more chaotropic agents.

Referring to FIG. 3A, the disposable cartridge 300 can include a first fluid pouch 302 and a second fluid pouch 304 attached to a first surface of an adjacent puncture layer 308 using a fluid pouch adhesive material 306. In some embodiments, the puncture layer 308 can include cut-outs for forming one or more of the alignment holes 338, mounting holes 336, and the access port 334. In some embodiments, the cut-outs for forming each of the four alignment holes 338, and/or the cut-outs for forming each of the mounting holes 336 can extend through all of the layers of the disposable cartridge 300. For example, each of the plurality of layers of the disposable cartridge 300 can include circular or substantially circular cut-outs appropriately sized for forming the alignment holes 338 and mounting holes 336.

A first surface of a fluid via layer 312 can be adhered to a second opposite surface of the puncture layer 308 using a puncture layer adhesive material 310. In some embodiments, the fluid via layer can include one or more openings for providing fluid communication between the first fluid pouch 302 and a fluid channel between the first fluid pouch 302 and the access port 334, and/or between the second fluid pouch 304 and a fluid channel between the second fluid pouch 304 and the access port 334.

A first surface of fluid path layer 316 can be adhered to a second opposite surface of the fluid via layer 312 using a first fluid path adhesive layer 314. A first surface of a bottom layer 320 can be adhered to a second surface of the fluid path layer 316 opposite the surface adhered to the fluid via layer 312, for example using a second fluid path adhesive layer 318. In some embodiments, the first fluid path adhesive layer 314, the fluid path layer 316, and the second fluid path adhesive layer 318 can include one or more cut-outs for forming one or more fluid channels such that the first fluid pouch and/or the second fluid pouch can be in fluid communication with the access port. In some embodiments, bottom layer 320 does not include corresponding cut-outs for forming one or more fluid channels such that the bottom layer 320 can facilitate sealing of the fluid channels. In some embodiments, the bottom layer 320 includes one or more openings for providing fluid communication between the fluid channels and one or more fluid chambers defined by subsequent layers of the disposable cartridge 300 (e.g., layer 322 through 332).

As shown in FIG. 3A, the disposable cartridge 300 can include one or more structural layers for defining the first fluid chamber beneath and in fluid communication with the first fluid pouch 302, and the second fluid chamber beneath and in fluid communication with the second fluid pouch 304. For example, the disposable cartridge 300 can include a first structural layer 324, a second structural layer 328 and a third structural layer 332, defining a shape and/or dimension (e.g., a height, length, and/or diameter) of the first and second fluid chambers. FIG. 3A shows a first and second fluid chamber having a circular or substantially circular shape. Other shapes may also be suitable, including for example, oval and/or rectangular. The first structural layer 324 can be adhered to a second surface of the bottom layer 320 opposite the surface of the bottom layer 320 adhered to the fluid path layer 316, for example using a first structural adhesive layer 322. The second structural layer 328 can be adhered to the first structural layer 324 using a second structural adhesive layer 326, and the third structural layer 332 can be adhered to the second structural layer 328 using a third structural adhesive layer 330. More or fewer structural layers may also be suitable. A thickness of each of the structural layers and/or a number of structural layers can be selected based on a desired dimension of the fluid chambers (e.g., a height, for example to provide a desired fluid chamber volume).

Figure 4A:
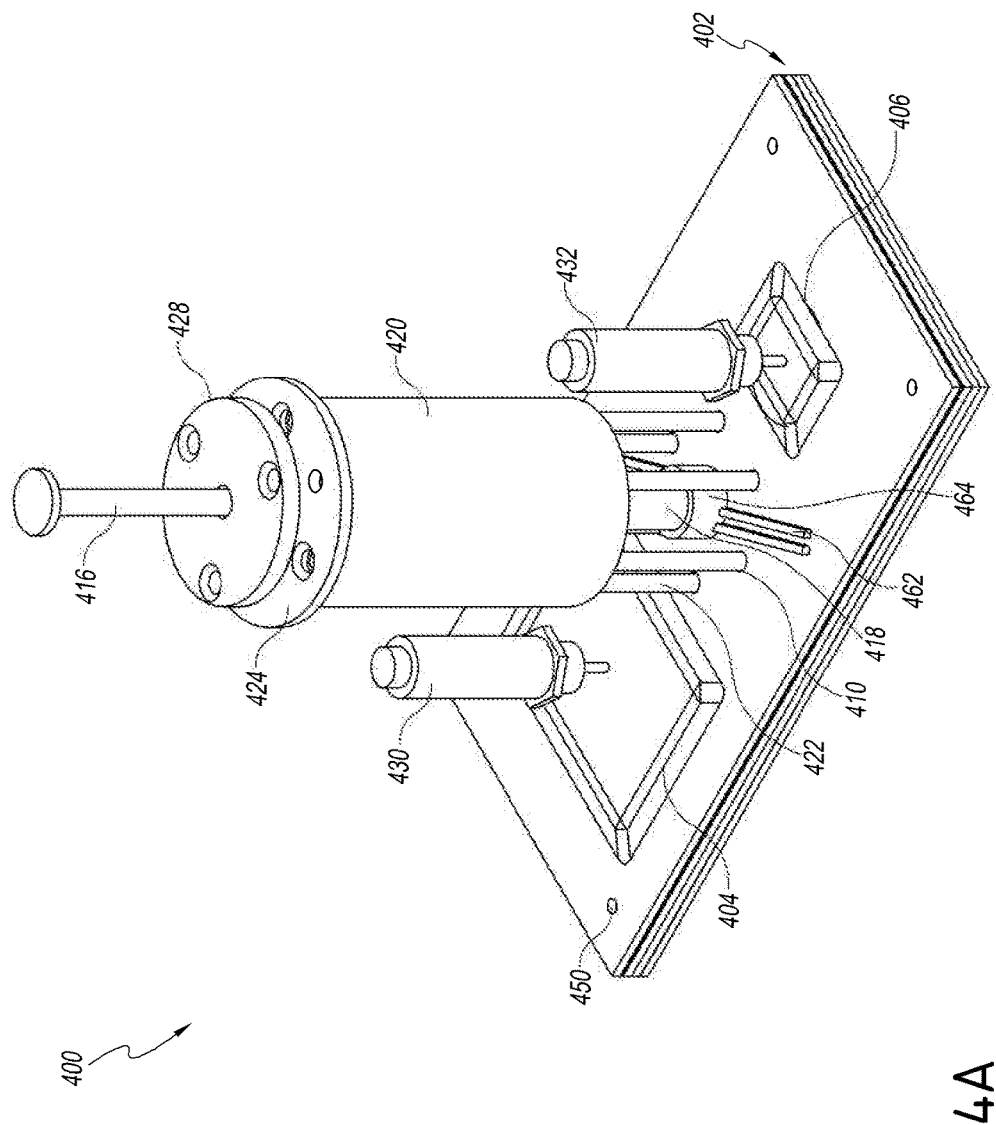
FIGS. 4A through 4C show an example of a purification apparatus.

FIG. 4A shows a perspective view of an example of a purification apparatus 400 including a disposable cartridge 402 and a syringe 412 (not shown) coupled to the disposable cartridge 402 using an assembly including a syringe holder 420 mounted onto the disposable cartridge 402 by securing a plurality of mounting fixtures 422 in corresponding mounting holes 410 of the disposable cartridge 402, and a first mounting bracket 424 and a second mounting bracket 428 to facilitate holding the syringe 412 in place.

In some embodiments, the disposable cartridge 402 can have a configuration similar to the configuration of the disposable cartridge 102 (as shown in FIGS. 1A and 1B). For example, the disposable cartridge 402 can include a first fluid pouch 404 for holding a quantity of a first reagent and a second fluid pouch 406 for holding a quantity of a second reagent, the first fluid pouch 404 and the second fluid pouch 406 in fluid communication with an access port of the disposable cartridge 402. The access port can be in fluid communication with a silica based membrane (SBM) containing compartment 418 coupled to an orifice at a distal end of the syringe 412 such that the syringe 412 can be used to apply a suction force and/or an expulsion force upon the first reagent and/or the second reagent. The purification apparatus 400 can include a first actuator 430 for applying a controlled force upon the first fluid pouch 404 to facilitate puncturing of the first fluid pouch 404 and a second actuator 432 for applying a controlled force upon the second fluid pouch 406 to facilitate puncturing of the second fluid pouch 406, for example to facilitate infusion into and/or withdrawal of fluid from the fluid pouches when an expulsion force and/or a suction force is applied by the syringe 412, respectively. For example, a first reagent from the first fluid pouch 404 and/or a second reagent from the second fluid pouch 406 can be drawn into the SBM containing compartment 418 and over the SBM using the syringe 412. In some embodiments, the disposable cartridge 402 does not include valves for controlling flow of fluid into and/or out of a fluid pouch and/or chamber (e.g., a valveless disposable cartridge 402).

In some embodiments, the purification apparatus 400 can include a heater 462 for heating the silica based membrane (SBM) containing compartment 418 such that the SBM in the compartment 418 may be heated to a desired temperature for drying the SBM. In some embodiments, the heater 462 can include a circumferential portion 464 for heating a sidewall of the SBM containing compartment 418. A height and/or a shape of the circumferential portion 464 can be selected to apply desired heating to the SBM and/or the SBM containing compartment 418. The heater 462 can include a resistive heating element and/or any other suitable heating technology. In some embodiments, the purification apparatus 400 can include one or more temperature sensors (e.g., thermal transducers) for sensing a temperature of the heater, the heated SBM and/or the heated SBM containing compartment 418, for facilitating controlled heating.

Figure 4B:
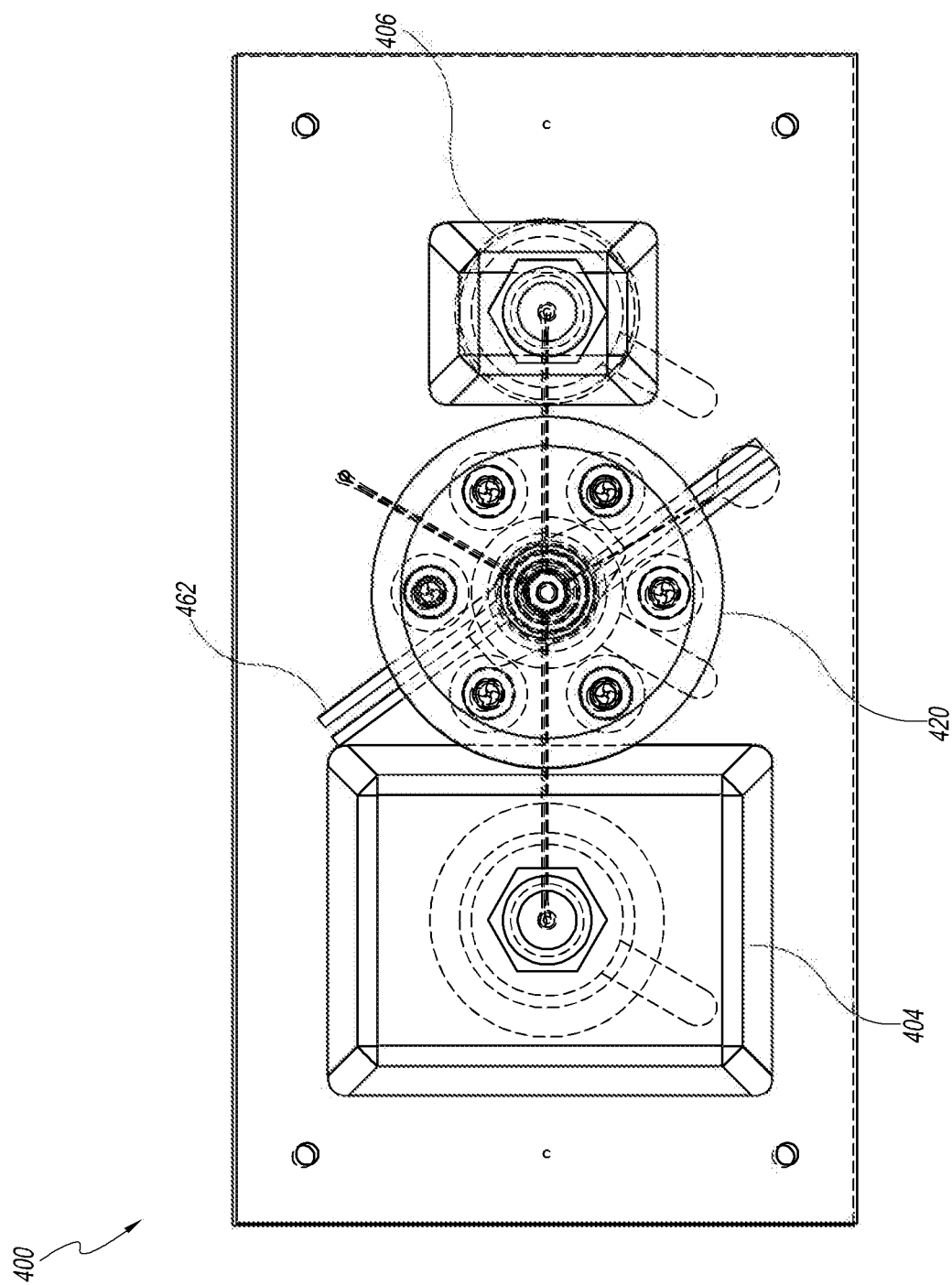
Figure 4C:
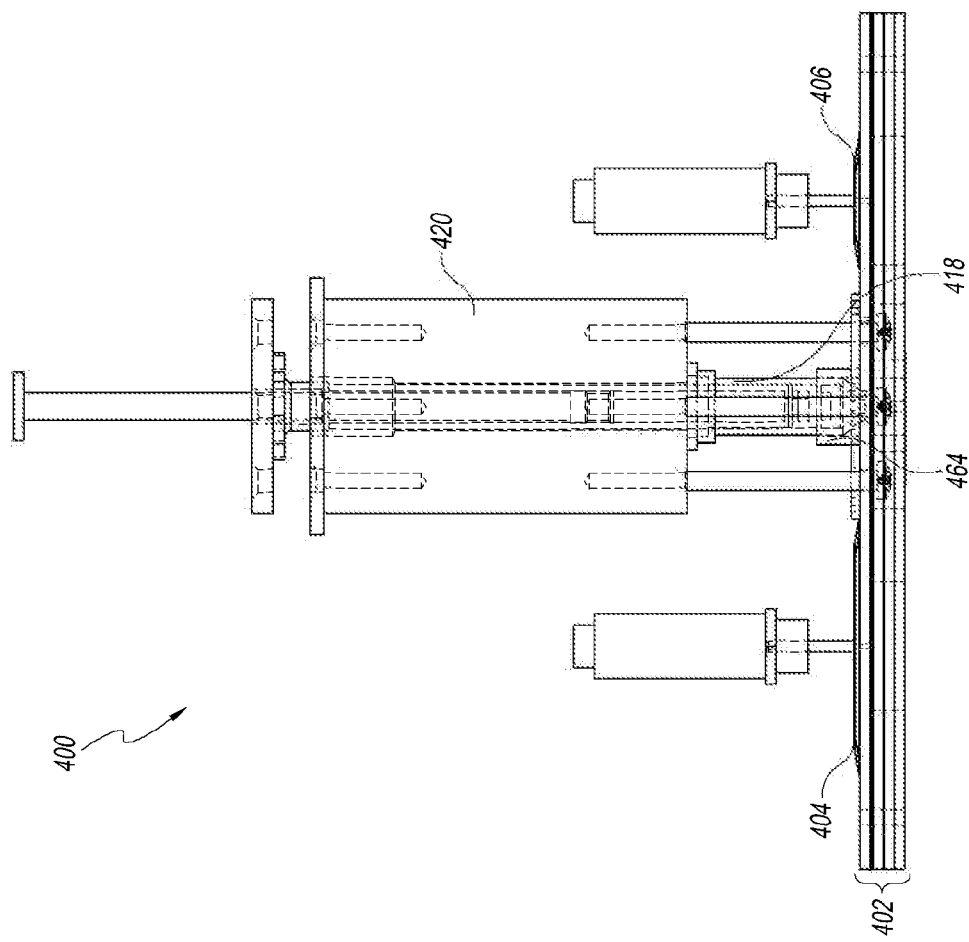

FIG. 4B shows a top-down plan view of the purification apparatus 400 and FIG. 4C shows a side view of the purification apparatus 400. A portion of the heater 462 is shown in the top-down plan view. In FIG. 4C, the circumferential portion 464 of the heater 462 is shown. The circumferential portion 464 can cover a portion of the sidewall of the silica based membrane (SBM) containing compartment 418.

Figure 5A:
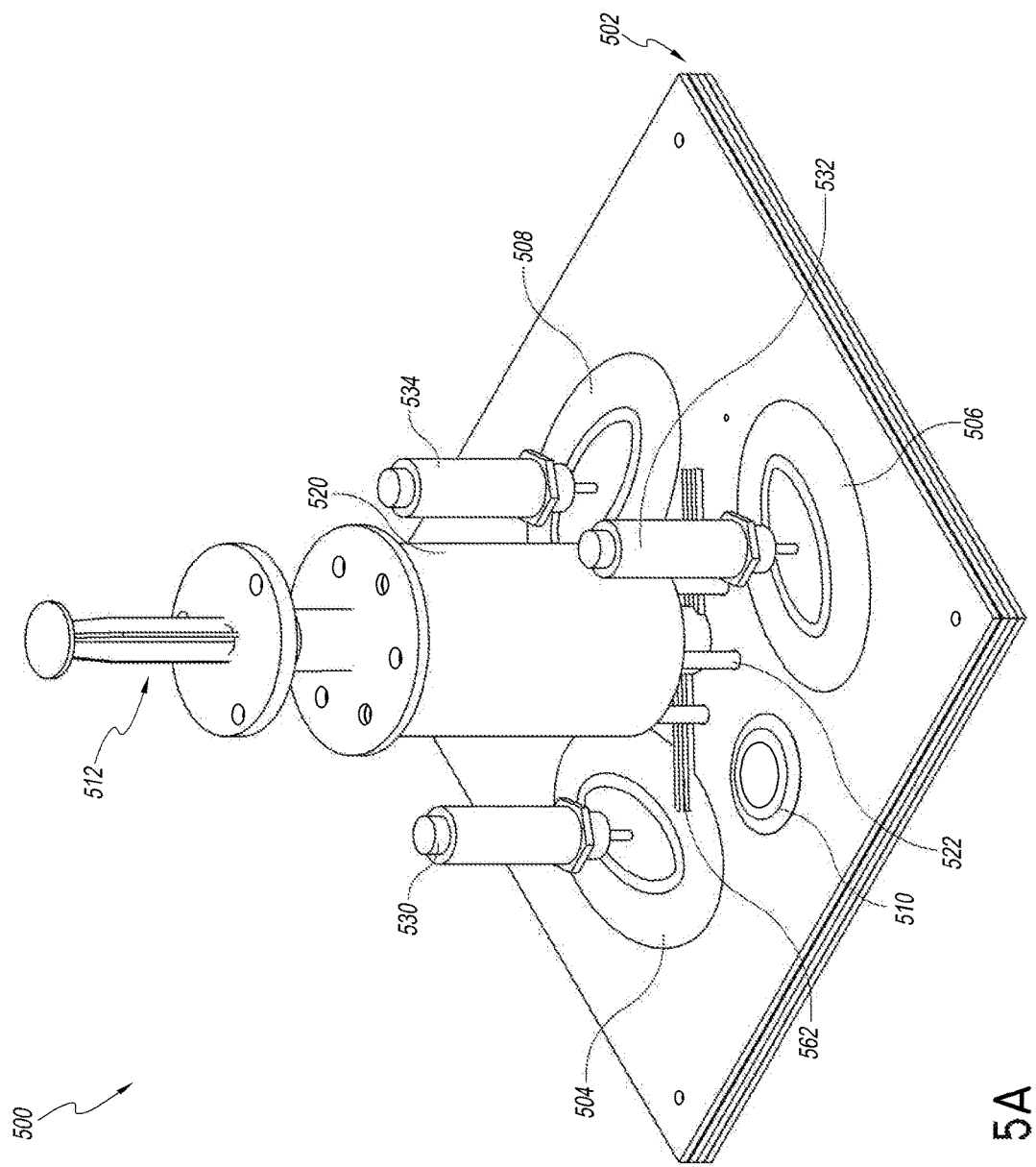
FIGS. 5A through 5C show an example of a purification apparatus.
Figure 5B:
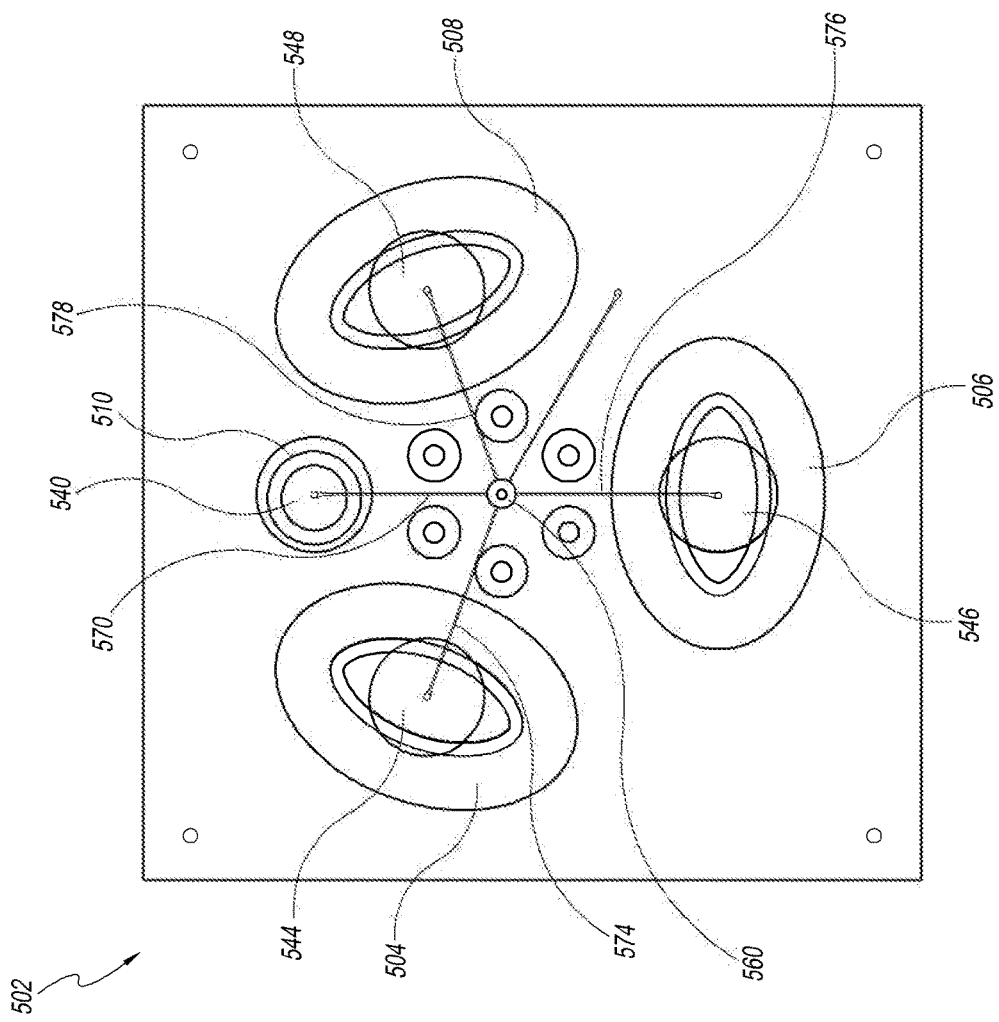
Figure 5C:
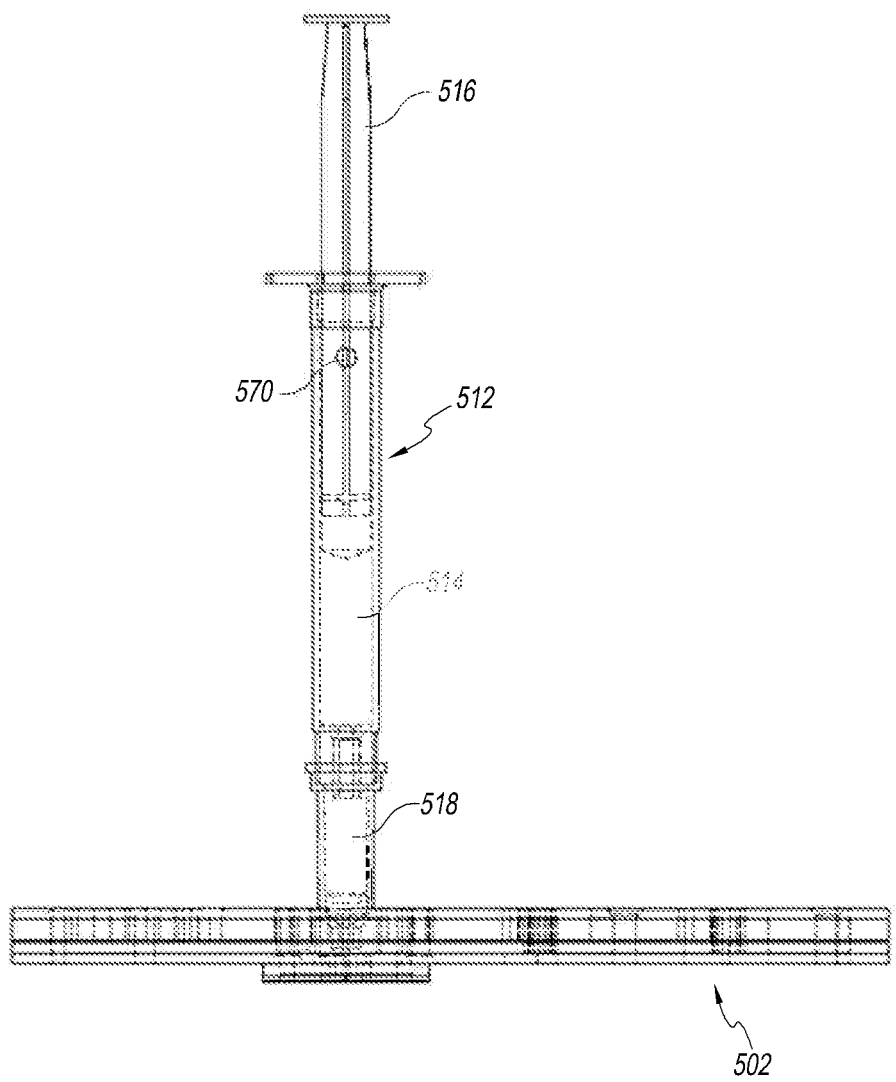

FIGS. 5A, 5B and 5C show various views of another example of a purification apparatus 500. FIG. 5A shows a perspective view the purification apparatus 500. The purification apparatus 500 can include a disposable cartridge 502 coupled to a syringe 512 using a syringe holder 520 mounted onto the disposable cartridge using a plurality of mounting fixtures 522. The disposable cartridge 502 can have a square or substantially square shape, and can include a first fluid pouch 504, a second fluid pouch 506 and a third fluid pouch 508 in fluid communication with an access port 560 (shown in FIG. 5B) on a first surface of the disposable cartridge 502. In some embodiments, the disposable cartridge 502 can include an elution fluid pouch 510 in fluid communication with the access port 560. An opening at a distal end of a silica based membrane (SBM) containing compartment 518 (shown in FIG. 5C) can be coupled to the access port 560 and an opening at a proximal end of the SBM containing compartment 518 can be coupled to an a distal orifice of the syringe 512. The purification apparatus 500 can include a heater 562 for heating the SBM containing compartment 518 for drying the SBM, for example for evaporating a reagent fluid.

The purification apparatus 500 can include a corresponding actuator configured to apply a controlled pressure for puncturing each of the first, second and third fluid pouches 504, 506, 508. In some embodiments, an actuator can be used for puncturing the elution fluid pouch 510. For example, the disposable cartridge 502 may not include any valves for controlling flow of fluid into and/or out of a fluid pouch.

FIG. 5B shows a top-down plan view of the disposable cartridge 502. FIG. 5B shows the first fluid pouch 504, the second fluid pouch 506, the third fluid pouch 508, and the elution fluid pouch 510 in fluid communication with the access port 560. The disposable cartridge 502 can include a first fluid chamber 544 in fluid communication with the first fluid pouch 504, a second fluid chamber 546 in fluid communication with the second fluid pouch 506, a third fluid chamber 548 in fluid communication with the third fluid pouch 508, and/or an elution fluid chamber 540 in fluid communication with the elution fluid pouch 510. For example, the first fluid chamber 544, the second fluid chamber 546, the third fluid chamber 548, and/or the elution fluid chamber 540 can be beneath the first fluid pouch 504, the second fluid pouch 506, the third fluid pouch 508, and/or the elution fluid pouch 510, respectively (e.g., as viewed from the first surface of the disposable cartridge 502). In some embodiments, the first fluid chamber 544, the second fluid chamber 546, the third fluid chamber 548, and/or the elution fluid chamber 540 are in fluid communication with the access port 560 via a first fluid channel 574, a second fluid channel 576, a third fluid channel 578, and/or an elution fluid channel 570, respectively. For example, the first fluid channel 574, the second fluid channel 576, the third fluid channel 578, and/or the elution fluid channel 570 can also be in fluid communication with the first fluid pouch 504, the second fluid pouch 506, the third fluid pouch 508, and/or the elution fluid pouch 510, such that fluid can be drawn simultaneously or substantially simultaneously from the first fluid pouch 504 and the first fluid chamber 544, the second fluid pouch 506 and the second fluid chamber 546, the third fluid pouch 508 and the third fluid chamber 548, and/or the elution fluid pouch 510 and the elution fluid chamber 540, when a suction force applied using the syringe 512.

FIG. 5C shows a side view of the syringe 512, SBM containing compartment 518, and disposable cartridge 502 of the purification apparatus 500. Referring to FIG. 5C, the syringe 512 can include a syringe barrel 514 and a syringe plunger 516 in the syringe barrel 514 configured to move in a proximal and/or distal direction relative to the syringe barrel 514 to apply a negative force and/or a positive force, respectively. In some embodiments, the syringe barrel 514 can include one or more air vents 570. The air vent 570 can facilitate drying of the silica based membrane (SBM) in the SBM containing compartment 518, provide pressure relief for the disposable cartridge 502 and/or facilitate release of volatile byproducts from the purification apparatus 500. For example, ambient air can be drawn into the syringe 512 through an air vent 570 and the air drawn into the syringe 512 can be subsequently delivered to the SBM in the SBM containing compartment 518 when the air is expelled from the syringe into the SBM containing compartment 518 by applying a positive force using the syringe plunger 516. Air can be repeatedly drawn into the syringe 512 for delivery over the SBM to facilitate air-drying of the SBM. In some embodiments, the air vent 570 can be fitted with an air filter, for example to prevent or substantially prevent escape of analyte sample through the air vent 570. Suitable air vent filter materials can include various polymeric materials, for example polyurethane and/or various other commercially available air filter materials (e.g., including filter materials available from Porex Filtration of Fairburn, Ga.).

Figure 6A:
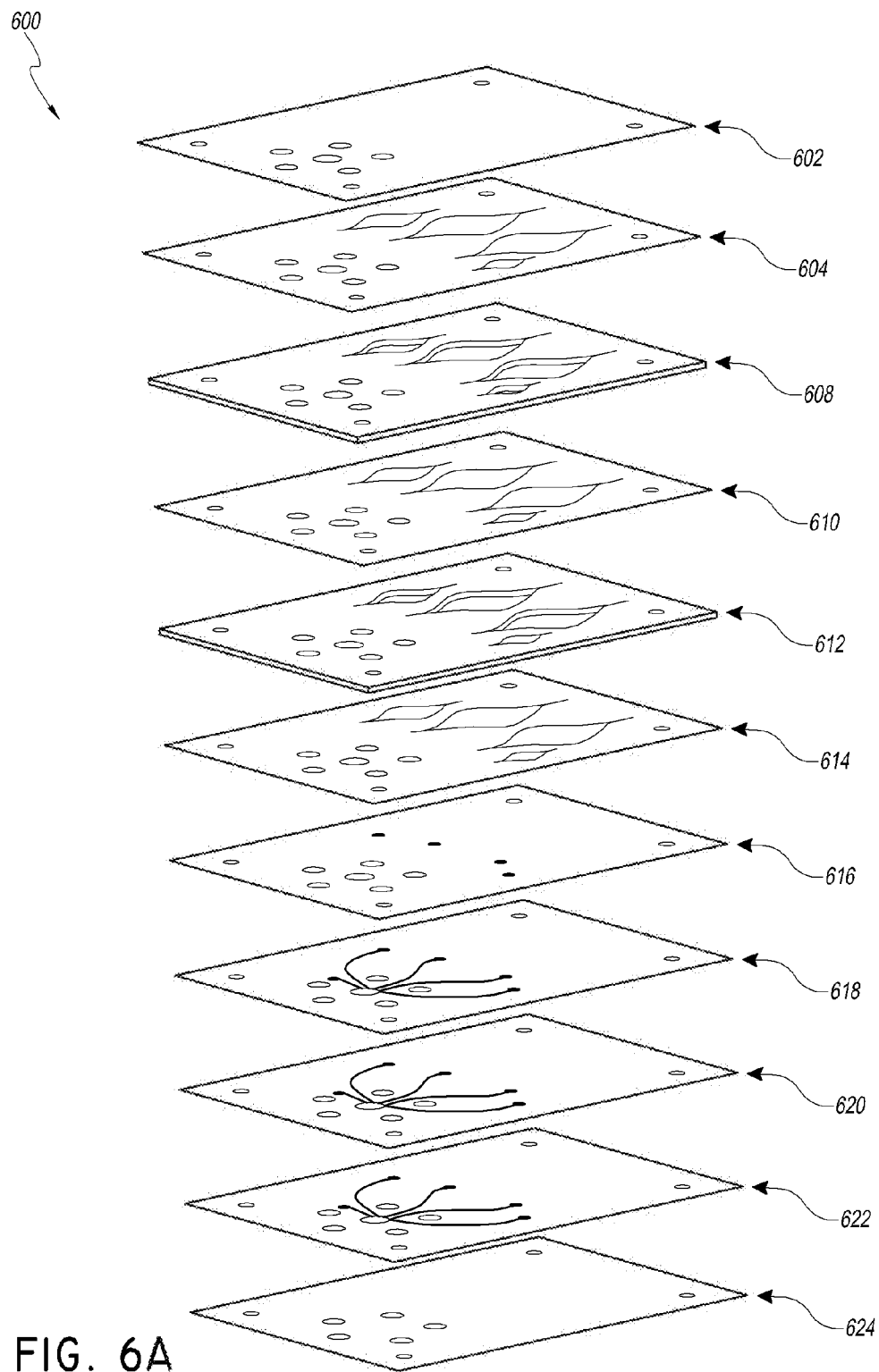
FIGS. 6A and 6B show an example of a disposable cartridge of a purification apparatus.
Figure 6B:
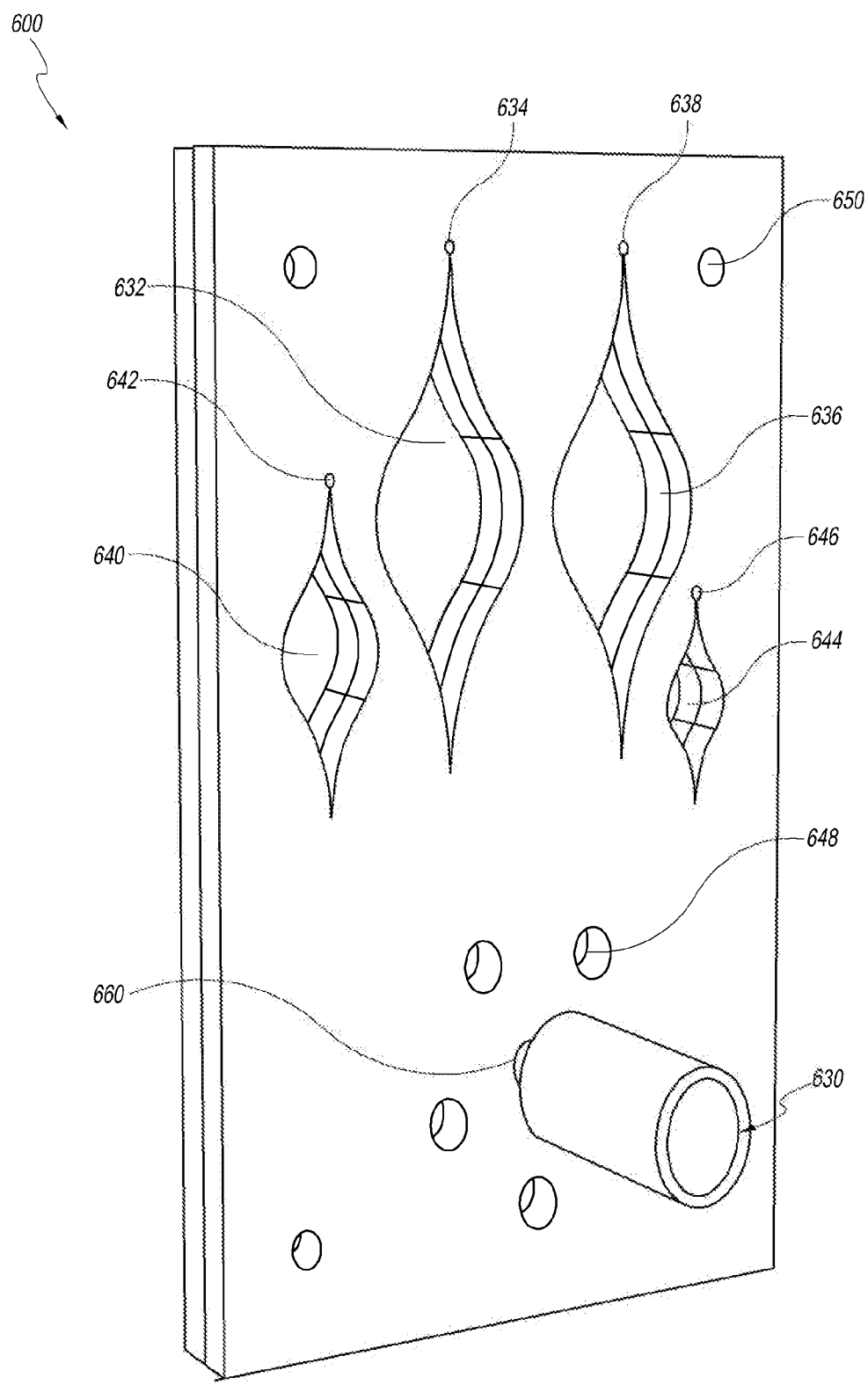

FIG. 6A shows an exploded view of an example of a disposable cartridge 600, and FIG. 6B shows a perspective view of a partially assembled disposable cartridge 600. As described herein, disposable cartridges can have a layered configuration, such that the disposable cartridges can be made from a plurality of layers of materials having cut-outs of various shapes (e.g., cut-outs having shapes and/or sizes for forming one or more features of the cartridge), where the plurality of layers can be joined together by adhesive material adjacent to each of the plurality of layers (e.g., by using a converter tape process). FIGS. 6A and 6B show that the adjacent layers of the disposable cartridge 600 can be adhered to one another to form an assembled disposable cartridge 600 including a first reagent chamber 632 and a second reagent chamber 636, an analyte chamber 640 and an elution fluid chamber 644 in fluid communication with an access port 660. For example, one or more layers of the disposable cartridge 600 can include one or more cut-outs having a shape and/or size configured for forming the first reagent chamber 632, the second reagent chamber 636, the analyte chamber 640 and/or the elution fluid chamber 644. FIG. 6B shows that, in some embodiments, the access port 660 of the disposable cartridge 600 can be coupled to a silica based membrane (SBM) containing compartment 630, such that the SBM container can be in fluid communication with the first reagent chamber 632, the second reagent chamber 636, the analyte chamber 640 and/or the elution fluid chamber 644. A suitable material for one or more layers of the disposable cartridge 600 and/or the SBM containing compartment 630 can be selected based on compatibility with the analyte solution and/or one or more reagent solutions. In some embodiments, one or more layers of the disposable cartridge 600 can be made of a suitable polymeric material. For example, multiple polymeric layers can be stacked together to provide a disposable cartridge having a desired mechanical rigidity and/or durability.

In some embodiments, one or more of the first reagent chamber 632, the second reagent chamber 636, the analyte chamber 640 and/or the elution fluid chamber 644 can include a chamber vent 634, 638, 642, 646, respectively. For example, a chamber vent can be opened for facilitating withdrawal of fluid from the chamber, and the chamber vent can be closed to facilitate retention of fluid within the chamber and/or prevent or substantially prevent release of fluid from the chamber, such as to provide a disposable cartridge 600 without valves for controlling extraction and/or delivery of fluid. In some embodiments, a chamber vent can be opened by applying a force to puncture the chamber vent. In some embodiments, a chamber vent can be closed by applying an adhesive material to seal the chamber vent (e.g., a pressure sensitive adhesive material). Other methods of opening and/or closing a chamber vent may also be suitable. In some embodiments, a chamber vent can be opened to allow a reagent solution to be withdrawn from the chamber (e.g., for flowing over a silica based membrane in fluid communication with the sealed after a previously used reagent solution (e.g., waste) is delivered back into the chamber (e.g., a reagent solution which has been passed over). Waste from each step is sent back to the same supply chamber by applying positive pressure and the punctured vents are sealed with a pressure sensitive tape for containment before proceeding with puncturing next vent. During the elution step, the eluent was collected in for further analysis.

In some embodiments, the disposable cartridge 600 can include a plurality of mounting holes 648 (e.g., six mounting holes 648 evenly spaced or substantially evenly spaced around the access port 660) for coupling a syringe assembly to the disposable cartridge 600, and a plurality of alignment holes 650 (e.g., four alignment holes 650 in each of the four corners of the rectangular or substantially rectangular disposable cartridge 600) for facilitating alignment with one another of the plurality of layers of the disposable cartridge 600. The mounting holes 648 and the alignment holes 650 may extend through the entire height of the disposable cartridge 600.

Referring to FIG. 6A, the disposable cartridge 600 can include a top layer adjacent a chamber layer, where the top layer is adhered onto the adjacent chamber layer through a chamber adhesive layer. The disposable cartridge 600 can include more than one chamber layer. For example, the disposable cartridge 600 can include a second chamber layer including a second chamber layer. As shown in FIG. 6A, the first chamber layer and the second chamber layer can include cut-outs corresponding to the shapes of the various fluid chambers of the disposable cartridge (e.g., cut-outs corresponding to the sample fluid chamber, the first reagent solution chamber, the second reagent chamber, and the elution fluid chamber, as shown in FIG. 6B).

A first surface of a fluid path via layer can be adhered to a second surface of the second chamber layer, for example by using a second chamber adhesive material. A first surface of the fluid path layer can be adhered to a second surface of the fluid path via layer opposite that adhered to the second chamber layer. The fluid path layer can be adhered to the fluid path via layer using a fluid path adhesive layer. A first surface of a bottom layer can be adhered to a second surface of the fluid path layer, for example by the second fluid path adhesive layer.

The fluid path via layer and fluid path adhesive layers can include one or more openings to provide fluid communication between a fluid chamber and a corresponding fluid channel such that the fluid chamber is in fluid communication with the access port. The fluid path layer includes cut-outs for the various channels providing fluid communication between the fluid chambers and the access port. As shown in FIG. 6A, the fluid path layer and/or the fluid path adhesive layers can include one or more cut-outs corresponding to the fluid channels providing fluid communication between the analyte chamber, the first reagent chamber, the second reagent chamber and/or the elution fluid chamber and the access port.

The second fluid path adhesive layer can include cutouts corresponding to the various channels between the access port and the chambers. The bottom layer can provide a seal for the channels such that the layer is solid where the channels are. For example, the bottom layer includes only cutouts for the mounting holes and the alignment holes.

Figure 7A:
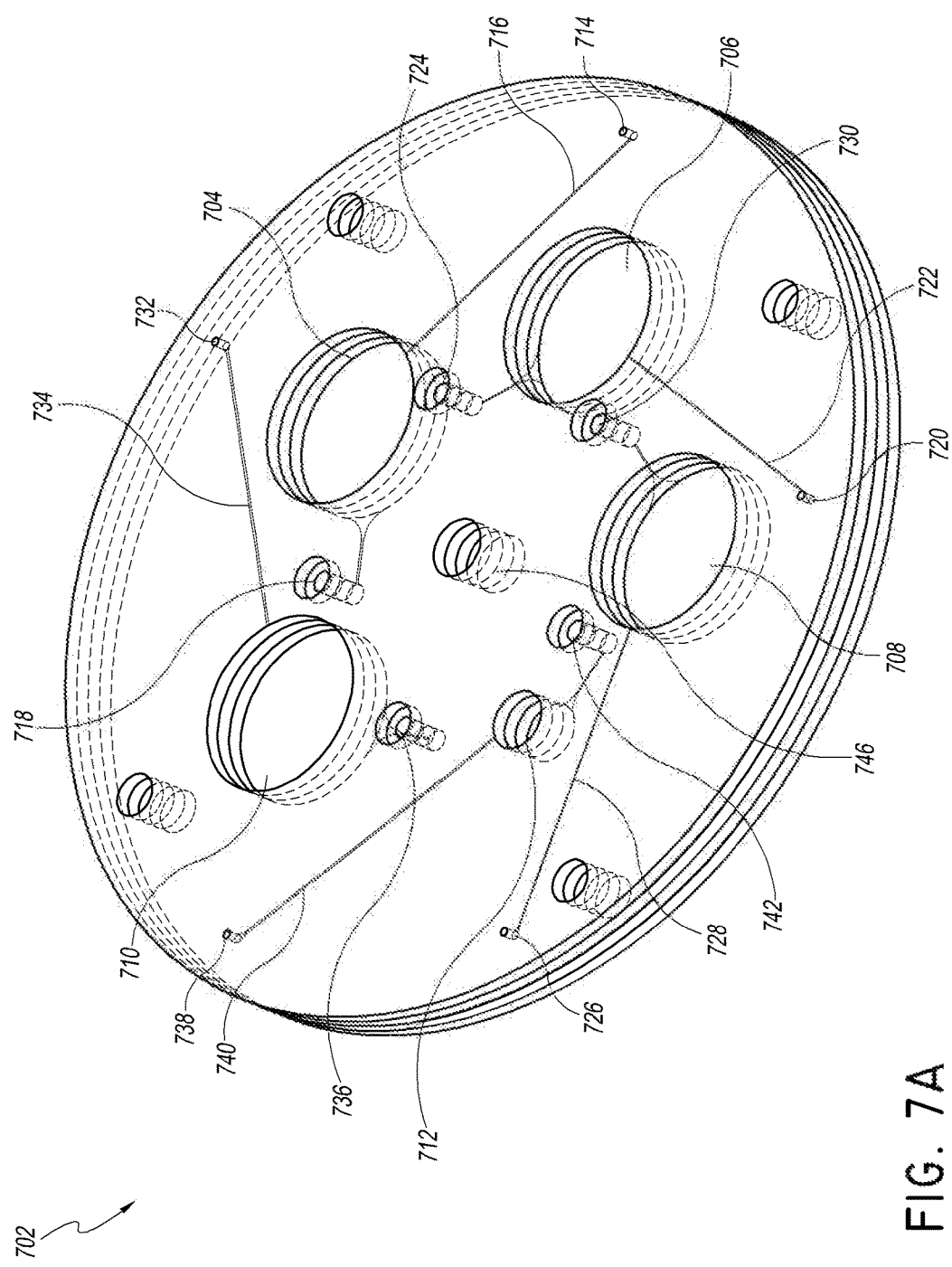
FIGS. 7A and 7B show an example of a disposable cartridge of a purification apparatus.

FIG. 7A shows a perspective view of a disposable cartridge 702. In some embodiments, the disposable cartridge 702 can have a circular or substantially circular shape and can be rotated around a pivot point, such a pivot point located at the center or substantially the center of the disposable cartridge 702 (e.g., the pivot point can be located within the center hole 746). The disposable cartridge 702 shown in FIG. 7A can include a first reagent chamber 704, a second reagent chamber 706, a third reagent chamber 708, and a fourth reagent chamber 708. More or fewer reagent chambers may also be suitable. In some embodiments, the disposable cartridge 702 includes an elution fluid chamber 712. In some embodiments, the disposable cartridge 702 can include more than one elution fluid chamber or can include no elution fluid chamber. The disposable 702 can be valveless and facilitate separation of respective reagent fluids and/or elution fluids by using separate chambers for reach fluid.

Referring to FIG. 7A, in some embodiments, the first reagent chamber 704 can be in fluid communication with a first reagent input port 714 via a first reagent input channel 716, such that a first reagent solution can be infused into the first reagent chamber 704 through the first reagent input port 714. In some embodiments, the first reagent solution can be extracted from the first reagent chamber 704 through the first reagent output port 718, for example by a syringe of the syringe assembly coupled to the disposable cartridge 702 at the center hole 746. The second reagent chamber 706, the third reagent chamber 708 and/or the fourth reagent chamber 710, can include respective input ports 720, 726, and 732, and input channels 722, 728, 734. In some embodiments, each of the second reagent chamber 706, the third reagent chamber 508 and/or the fourth reagent chamber 710, can include respective output ports 724, 730, 736, for facilitating extraction of the reagent solutions from the respective reagent chambers. In some embodiments, reagent solutions can be delivered into a reagent chamber through an output port of the reagent chamber.

In some embodiments, the disposable cartridge 702 includes an elution fluid chamber 712. The elution fluid chamber 712 can be in fluid communication with an elution fluid input port 538 via an elution fluid input channel 740 such that an elution fluid can be infused into the elution fluid chamber 712 through the elution fluid input port 738. In some embodiments, some or all of the elution fluid can be extracted from the elution fluid chamber through an elution fluid output port 742. In some embodiments, elution fluid can be delivered into the elution fluid chamber 712 through the elution fluid output port 742.

The disposable cartridge 702 can be coupled to an assembly for placing a syringe at a desired position relative to the disposable cartridge 702. For example, the disposable cartridge 702 can be coupled to the assembly through the center hole 746 such that the syringe can be rotated relative to the disposable cartridge 702, and/or the disposable cartridge 702 can be rotated relative to the syringe assembly. The syringe can be positioned over an output port of a disposable cartridge fluid chamber such that the syringe can be used to deliver fluid to and/or extract fluid from the fluid chamber (e.g., deliver a reagent fluid and/or an elution fluid to and/or withdraw the reagent fluid and/or elution fluid from the respective fluid chamber. For example, a syringe orifice at a distal end of the syringe can be in fluid communication with the input port. The syringe can be rotated relative to the disposable cartridge 702, and/or vice versa, around the center hole 746 such that the syringe can be positioned over a desired fluid chamber (e.g., the first reagent chamber, second reagent chamber, third reagent chamber, fourth reagent chamber, elution fluid chamber) for delivering fluid to and/or withdrawing fluid from the fluid chamber. The syringe and/or the cartridge 702 can be rotated around the center hole 746 such that a desired input port and/or output port can be coupled to the syringe for infusing or withdrawing fluid from the fluid chamber.

Figure 7B:
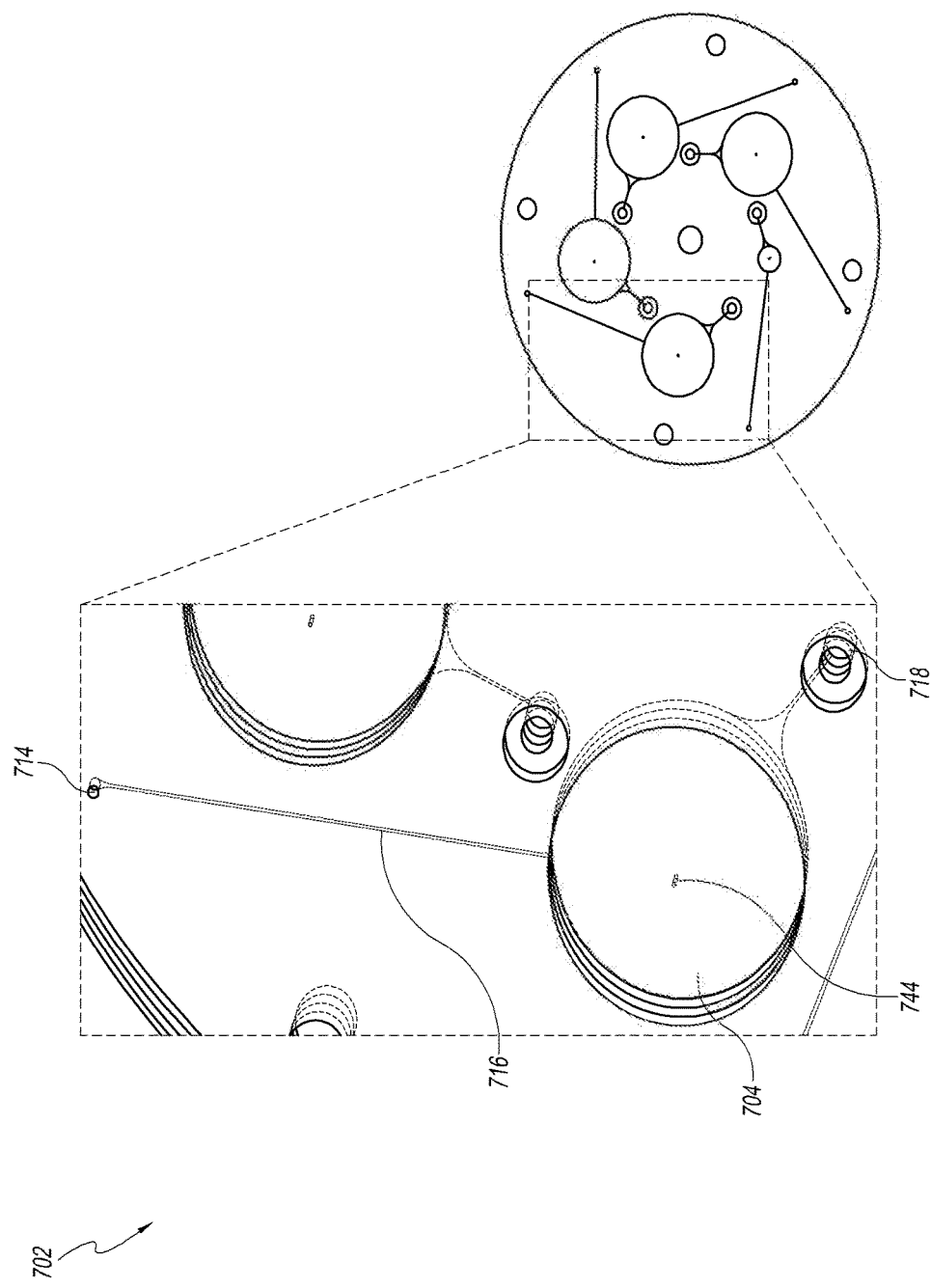

FIG. 7B shows a portion of the disposable cartridge 702 at a greater magnification. FIG. 7B shows that the first reagent chamber 704 can be in fluid communication with the first reagent input port 714 via a first reagent input channel 716, such that a first reagent solution can be infused into the first reagent chamber 704 through the first reagent input port 714. In some embodiments, the first reagent solution can be extracted from the first reagent chamber 704 through the first reagent output port 718, for example by a syringe of the syringe assembly coupled to the disposable cartridge 702 at the center hole 746. In some embodiments, each fluid chamber of the disposable cartridge 702 can include one or more chamber vents. For example, the first reagent chamber 704 can have a chamber vent 744 through which air can be passed into and/or out of the first reagent chamber 704. For example, a chamber vent can facilitate displaced air to be expelled from the chamber when fluid is infused into the chamber (e.g., when fluid is infused into the chamber through a fluid input port and/or a fluid output port), and can facilitate drawing of air into the chamber, for example to replace a fluid when the fluid is extracted from the chamber (e.g., when fluid is withdrawn from the chamber through the fluid output port). The chamber vent can be opened (e.g., through mechanical puncturing of the chamber vent, and/or any other suitable method) to facilitate infusion and/or withdrawal of air into and/or out of the chamber. In some embodiments, the chamber vent can be closed (e.g., by applying an adhesive material to the chamber vent, and/or by using any other suitable method) subsequent to infusion and/or withdrawal of fluid into the chamber, for example to prevent or substantially prevent fluid from leaving the chamber.

FIGS. 8A through 8D show an example of an assembly 800 for positioning a syringe 820 at a desired location over a disposable cartridge (e.g., the disposable cartridge 702 as shown in FIGS. 7A and 7B). The assembly 800 can include a mounting bracket 802 coupled to a syringe holder 810, the syringe holder 810 having a tubular space 812 through a central portion of the syringe holder 810 for retaining a syringe 820, and the assembly 800 can be configured to couple to a disposable cartridge using a center bolt 818 such that the assembly 800 can be rotated relative to the disposable cartridge around the center bolt 818, or vice versa (e.g. the disposable cartridge can be rotated relative to the assembly 800). For example, the assembly 800 can be rotated around the center bolt 818 such that the syringe 820 can be positioned at a desired location relative to the disposable cartridge.

FIG. 8A shows a side perspective view of a mounting bracket 802 coupled to a syringe holder 810 of the assembly 800. A distal portion of the syringe holder 810 can be coupled to the mounting bracket 802. For example, the mounting bracket 802 can have a plurality of mounting holes 808 on a first surface into which a corresponding plurality of mounting fixtures (e.g., mounting screws) 814 can be placed to secure the coupling between the distal portion of the syringe holder 810 and the mounting bracket 802. In some embodiments, a proximal portion of the syringe holder 810 can include a plurality of mounting fixture insertion openings 816, for example for placement of corresponding mounting fixtures when coupling one or more brackets onto the syringe holder 810 (e.g., brackets 832, 834 shown in FIG. 8C, such as for securing the syringe 820 within the syringe holder 810).

The mounting bracket 802 can include one or more alignment features to facilitate alignment of the assembly 800 relative to a disposable cartridge, alignment features such as two standoffs 804, 806 at equal distance on the mounting bracket 802 from the location at which the mounting bracket 802 couples to the syringe holder 810. More or fewer standoffs can be suitable, and/or the standoffs can be placed at other locations on the mounting bracket 802.

FIG. 8B shows a top down plan view of the assembly 800. FIG. 8B shows a syringe holder 810 coupled to a mounting bracket 802, and the mounting bracket 802 having two standoffs 804, 806 at an equal distance from the center bolt 818 and on opposing portions of the mounting bracket 802.

Figure 8D:
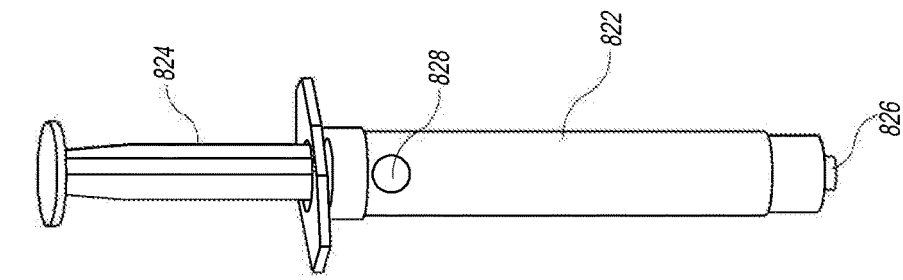
Figure 8C:
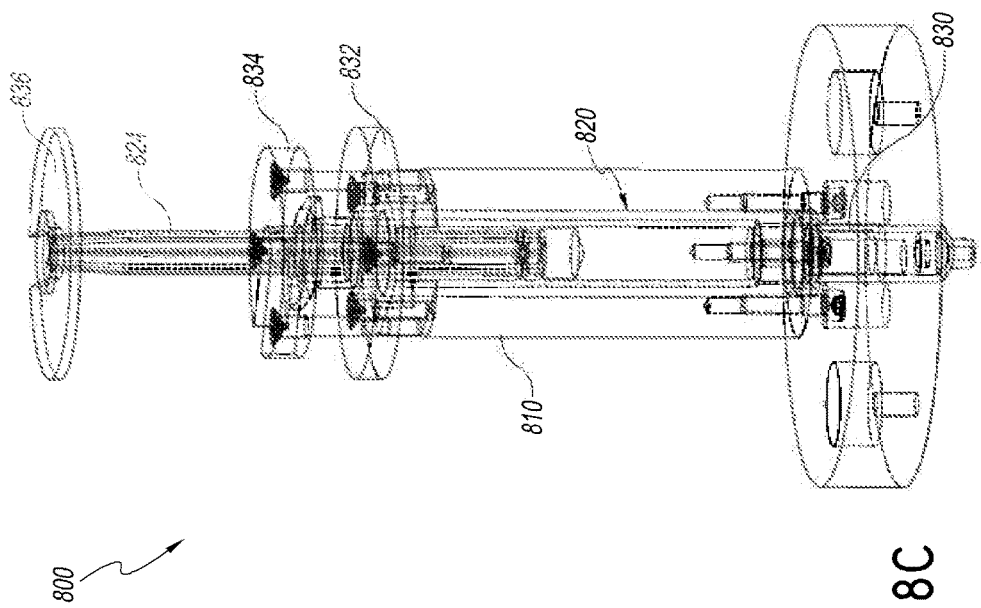

FIG. 8C shows a side perspective view of the assembly 800. In FIG. 8C, the syringe 820 is placed within the syringe holder 810. In some embodiments, the syringe 820 can be coupled to brackets 832, 834, for example to facilitate holding the syringe 820 in place within the syringe holder 810. A plunger 824 of the syringe 820 can be coupled to linear actuator adapter 836, for example to facilitate application of force upon the syringe plunger 824 by a linear actuator (e.g., the linear actuator as described herein with reference to FIG. 12).

As shown in FIG. 8C, in some embodiments, the syringe holder 820 can include a silica containing compartment 830 (e.g., silica membrane based (SBM) containing compartment, such as a container having a silica material embedded in and/or integrated as part of the container) at or proximate to a distal portion of the syringe holder 820. For example, the silica containing compartment 830 can be in fluid communication with the syringe 820. An opening at or proximal to a distal end of the silica containing compartment 830 can be configured to provide an interference fit with an fluid input port and/or output port of a disposable cartridge (e.g., a rotatable disposable cartridge) and/or the opening in the silica containing compartment 830 can be coupled to the access port of the disposable cartridge using a sealing ring (e.g., an O-ring) for providing desired coupling between the input and/or output port and the opening of the silica containing compartment 830.

In some embodiments, the center bolt 818 in the mounting bracket 802 can be inserted into a corresponding center hole of a rotatable disposable cartridge. For example, the disposable cartridge can be rotated around its center, the rotating disposable cartridge can index a desired fluid chamber and/or fluid pouch by placing the desired fluid chamber and/or fluid pouch output port below the opening at a distal portion of the silica containing compartment, and the output port of the desired fluid chamber and/or fluid pouch can be raised into contact with the opening in the silica containing compartment 830 and the two disposable standoffs 804, 806. For example, a seal can be created where the disposable cartridge output port is coupled to the opening in the silica containing compartment 830, such as by tightening the coupling between the disposable cartridge and the assembly 800 (e.g., by tightening a wing nut on the center bolt 818). In some embodiments, the two standoffs 804, 806 can be used to facilitate alignment and/or proper sealing between the disposable cartridge output port and the opening in the silica containing compartment 830 by ensuring proper contact between the opening in the silica containing compartment 830 and standoffs 804, 806, of the assembly 800, and the disposable cartridge (e.g., ensure proper alignment and/or contact by contacting three points simultaneously on respective surfaces of the two components to be coupled and/or aligned). In some embodiments, an O-ring, plastic seal, or other suitable sealing method can be used to facilitate sealing between the assembly 800 and the disposable cartridges. The coupling between the disposable cartridge and the assembly 800 can be loosened for indexing other input and/or output ports of the disposable cartridge (e.g., the disposable cartridge can be lowered away from the assembly 800 by loosening the wingnut of the center bolt).

FIG. 8D shows an example of a syringe 820 of the assembly 800. The syringe 820 can include a syringe barrel 822 and a syringe plunger 824 within the syringe barrel 822. The syringe 820 can have an orifice 826 at its distal portion. For example, the orifice 826 can be in fluid communication with the silica containing compartment 830 when the syringe 820 is place within the syringe holder 820 of the assembly 800. In some embodiments, the syringe 820 can include an air vent 828 on a syringe barrel sidewall. The air vent 828 can facilitate drawing of air into the syringe 820, for example for passing air over the silica material (e.g., for drying of the silica material). In some embodiments, the air vent 828 includes a filter to prevent or substantially prevent nucleic acid from leaving the syringe 820. Suitable filter can include a variety of materials, including various polymeric materials (e.g., polyurethane, and/or various filter materials commercially available from Porex Filtration of Fairburn, Ga.).

Figure 9:
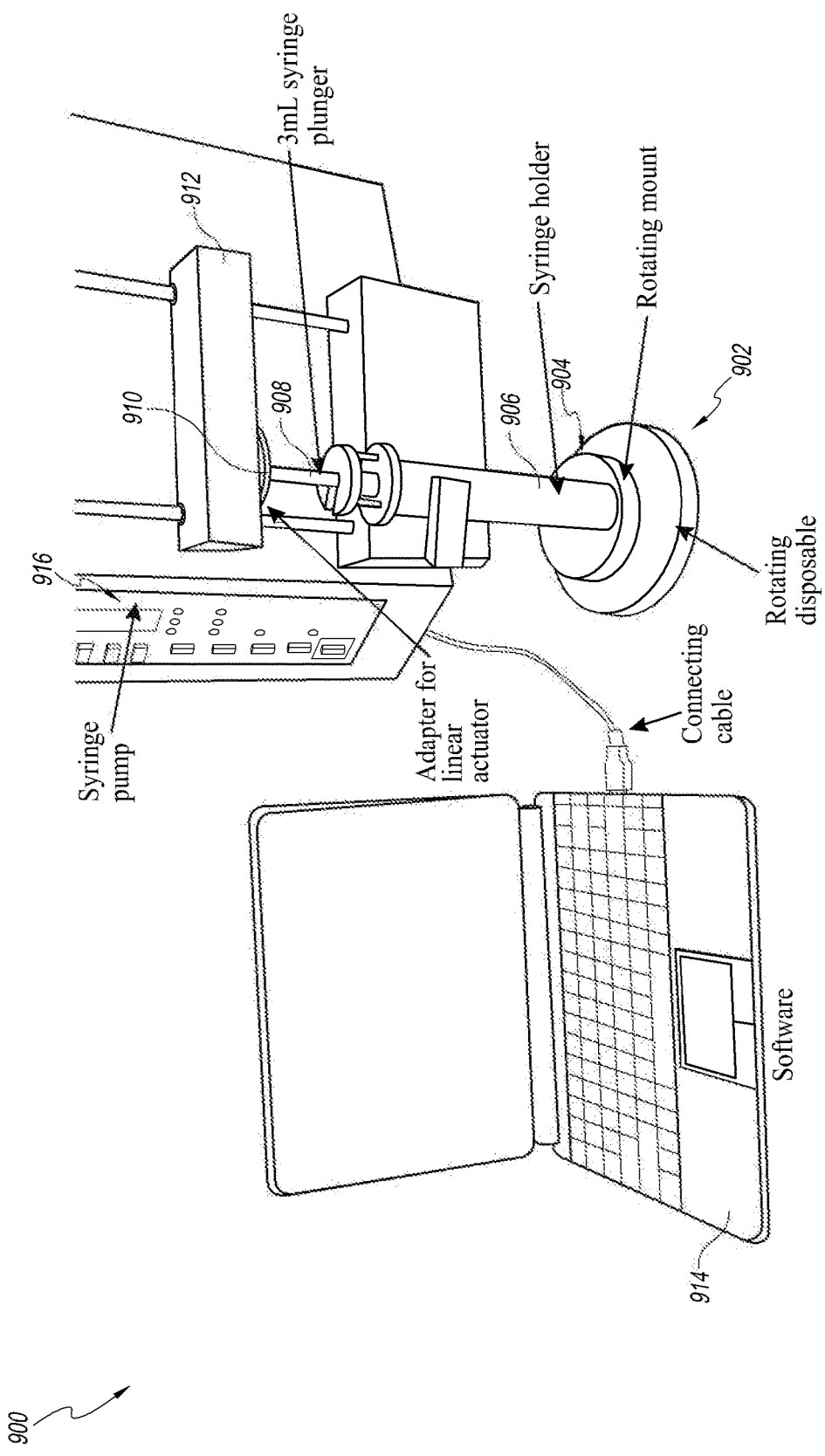
FIG. 9 shows an example of a purification apparatus.

FIG. 9 shows an example of a purification system 900 which includes a rotatable disposable cartridge 902 coupled to a rotatable assembly (e.g., similar to the assembly 800 shown in FIGS. 8A through 8C) including a mounting bracket 904 and a syringe holder 906. A syringe 908 can be placed in the syringe holder 906 for coupling with the disposable cartridge 902. The syringe 908 can be coupled to a linear actuator 912, for example through a linear actuator adaptor 910. Positive and/or negative force can be applied upon the syringe 908 by the syringe pump 916, for example by movement of the linear actuator 912. In some embodiments, a computer software 914 can be configured to the control linear actuator 912 coupled to the syringe pump 908. For example, fluid may be introduced into different fluid chambers and/or fluid porches of the disposable cartridge 902 through a corresponding input port as the disposable cartridge 902 is rotated relative to the mounting bracket 904.

Figure 10:
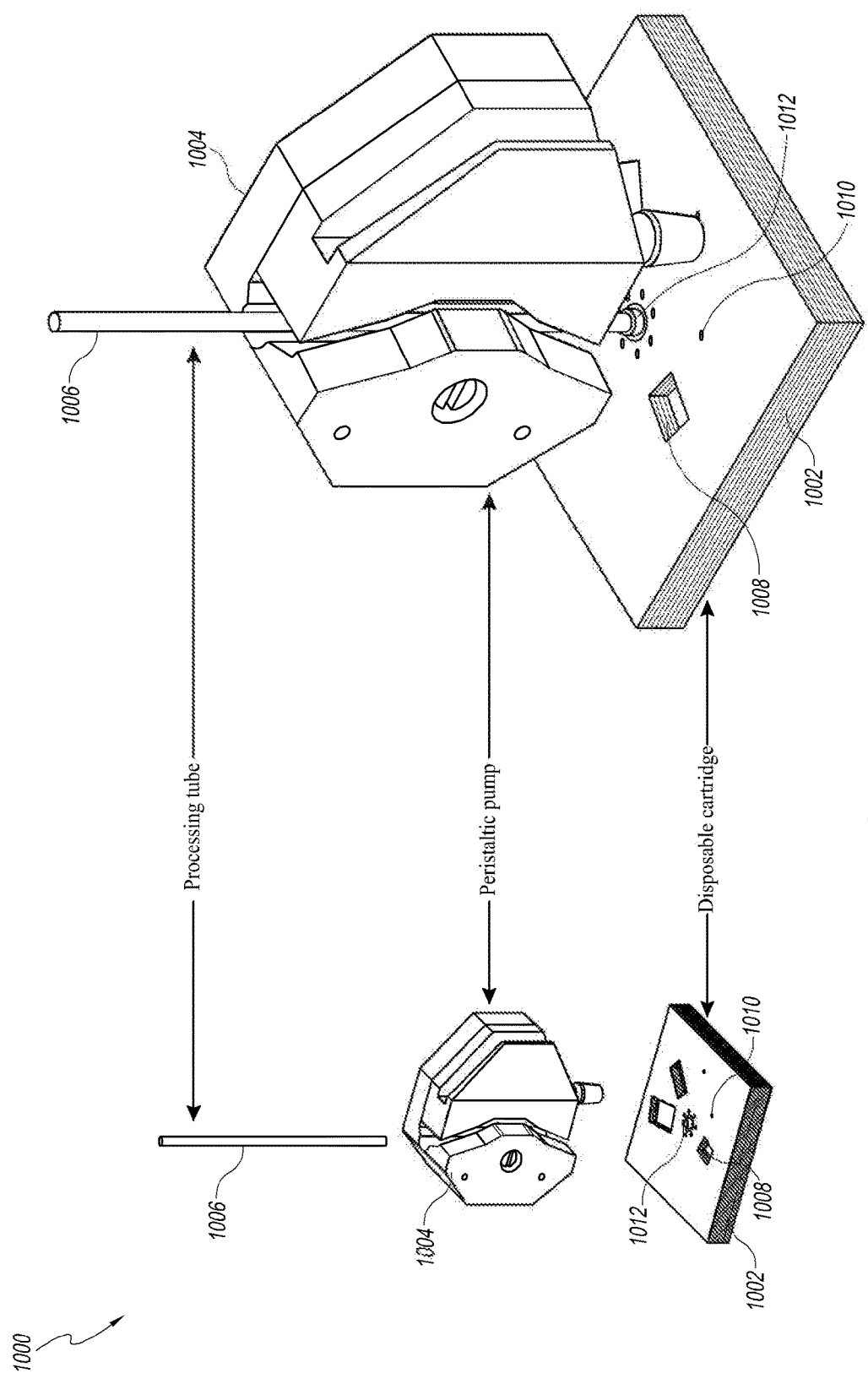
FIG. 10 shows an example of a purification apparatus which includes a pump.

FIG. 10 shows a purification apparatus 1000 including a valve-less disposable cartridge 1002 fitted with a pump (e.g., a peristaltic pump) 1004. The pump 1004 can provide positive and/or negative pressure for transporting fluids into and/or within the disposable cartridge 1002. In some embodiments, a processing tube 1006 can be used to fill and/or empty a chamber 1008 of the disposable cartridge 1002 using the pump 1004. The process tube 1006 may be made of a variety of suitable materials known in the art.

A chamber 1008 of the disposable cartridge 1002 can be filled with a fluid by coupling the processing tube 1006 of the pump 1004 to an access port 1012 of the disposable cartridge 1002, loading the fluid into the processing tube 1006 coupled the access port 1012, and activating the pump 1004 to apply a positive pressure (e.g., activating a peristaltic pump in a forward direction). The chamber 1008 can have an air vent 1010 which can be opened to facilitate exit of displaced air from the chamber 1008 through the air vent 1010 to facilitate filling of the chamber 1008 with the fluid. In some embodiments, the fluid can be extracted from the chamber 1008 through the process tube 1006 by activating the pump 1004 to apply a negative force (e.g., activating a peristaltic pump in a reverse direction). The air vent 1010 of the chamber 1008 can be opened to facilitate drawing of air into the chamber 1008, such as to replace the fluid extracted from the chamber 1008. In some embodiments, an air vent of one chamber in a disposable cartridge can be opened at a time (e.g., keeping air vents of other chambers closed) to facilitate control from which chamber fluid is extracted. For example, vacuum created by fluid displacement can prevent or substantially prevent fluid in the non-selected chambers (e.g., chambers having closed air vents) from leaving the non-selected chambers.

As described herein, the pump 1004 can be a peristaltic pump. Peristaltic pumps can be cost-effective, can facilitate provision of controlled and variable positive and/or negative pressure, can be robust, and/or can have a compact volume for portability in field deployable biomedical devices. In some embodiments, a peristaltic pump can facilitate isolation of sterile and/or aggressive fluids in a processing tube (e.g., the process tube may be a disposable tube), for example reducing contamination and/or corrosion due to exposure to the fluids. Other pumps may also be suitable. In some embodiments, one or more chambers of the disposable cartridge 1002 can be filled with and/or emptied of fluid using both the pump 1004 and/or one or more other suitable techniques known in the art for applying a positive and/or a negative pressure to a fluid in the chambers and/or fluid pouches (e.g., by using a syringe, as described herein). The various fluids originate from the different fluid chambers that can be filled manually through the fluid inlet/air vent or through the processing tube.

Figure 11A:
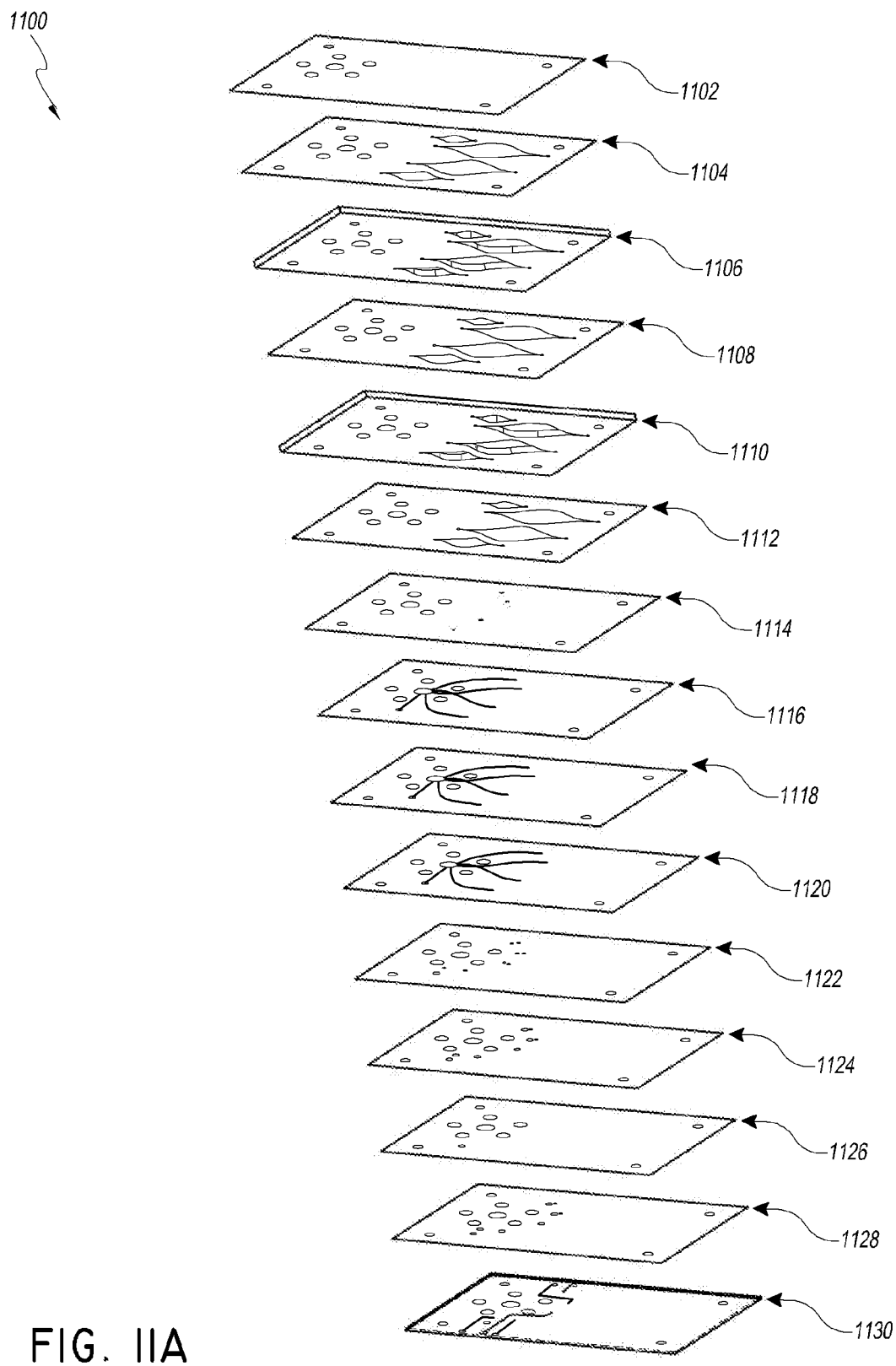
FIGS. 11A and 11B show an example of a disposable cartridge having a plurality of valves for controlling fluid flow into and/or within the disposable cartridge.
Figure 11B:
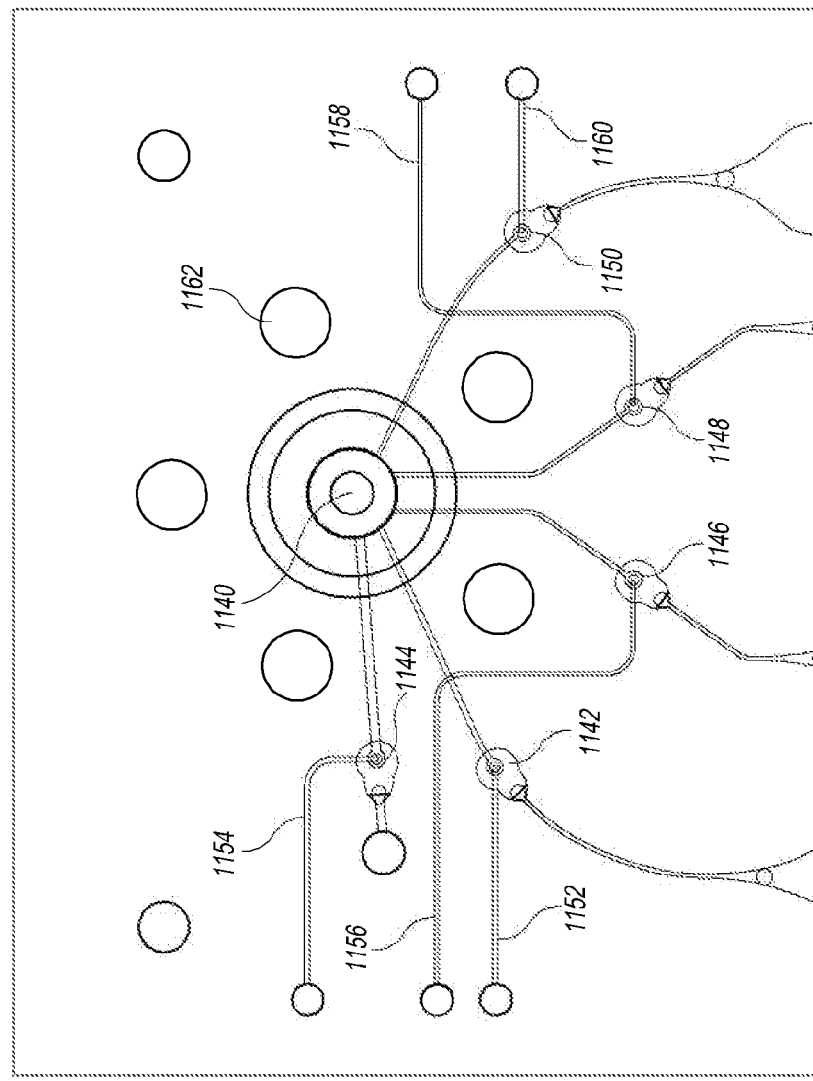

FIGS. 11A and 11B show an example of a disposable cartridge 1100 which can include one or more valves for controlling flow of fluid into, out from and/or within the disposable cartridge 1100. FIG. 11A shows an exploded view of the disposable cartridge 1100 and FIG. 11B shows a top down cross-section view of a portion of the disposable cartridge 1100. As shown in FIG. 11B, the disposable cartridge 1100 can include valves 1142, 1144, 1146, 1148, 1150 (e.g., pneumatic valves) for controlling flow of fluid through corresponding fluid channels which are in fluid communication with an access port 1140 of the disposable cartridge. For example, the disposable cartridge 1100 can have a valve on each fluid channel with pneumatic controls for actuation, such that each valve 1142, 1144, 1146, 1148, 1150, is coupled to a valve pressurization line 1152, 1154, 1156, 1158, 1160, respectively. A pressurization line can be activated for activating a corresponding valve. In some embodiments, a selected pneumatic valve can be activated to close a fluid channel by pinching off fluid flow when the valve is pressurized.

In some embodiments, a disposable cartridge having one or more valves for controlling fluid flow into, out from and/or within the cartridge, can advantageously facilitate processing of analyte solutions including nucleic acid using the disposable cartridge. For example, reagent fluids used in processing nucleic acid samples can include high alcohol content (e.g., nucleic acid binding and/or wash buffers used in nucleic acid purification), making fluid control difficult due, for example, to a low surface tension and/or high volatility of the reagent fluids.

The disposable cartridge 1100 can have a layered configuration, including a plurality of layers of materials having cut-outs of various shapes (e.g., cut-outs having shapes and/or sizes for forming one or more features of the cartridge) adhered together by adhesive material adjacent to each of the plurality of layers (e.g., by using a converter tape process). FIG. 11A shows that the disposable cartridge 1100 can include layers of materials having cut-outs similar to that of the layers of the disposable cartridge 600. For example, a top layer 1102 can be adhered onto an adjacent first chamber layer 1106 through a first chamber adhesive layer 1104. For example, the top layer 1102 can provide a seal for the chambers formed by the first chamber layer 1106. A second chamber layer 1110 can be adhered onto the first chamber layer 1106 using a second chamber adhesive layer 1108. A fluid path via layer 1114 can be adhered to the second chamber layer 1110 using a third chamber adhesive layer 1112. A fluid path layer 1118 can be adhered to the fluid path via layer 1114 using a first fluid path adhesive layer 1116. Layers for forming the valves can be beneath the layers for forming the fluid channels of the disposable cartridge 1100 (e.g., the fluid path layers), for example by adhering the valve layers using a second via path adhesive layer 1120.

The first chamber layer 1106, first chamber adhesive layer 1104, second chamber layer 1110, second chamber adhesive layer 1108, and third chamber adhesive layer 1112, can include cut-outs corresponding to various fluid chambers of the disposable cartridge 1100 (e.g., a sample fluid chamber, a first reagent solution chamber, a second reagent chamber, a elution fluid chamber). The fluid path via layer 1114, first fluid path adhesive layer 1116, fluid path layer 1118 and second fluid path adhesive layer 1120 can include cut-outs corresponding to various fluid channels of the disposable cartridge 1100 (e.g., fluid channels for providing fluid flow to a sample fluid chamber, a first reagent solution chamber, a second reagent chamber, and/or a elution fluid chamber).

Various layers for forming one or more of the valves can be beneath the layers for forming the fluid channels in the disposable cartridge 1100. For example, a valve via layer 1122 including various openings for providing fluid communication between the valves and the fluid channels of the disposable cartridge 1100 can be adhered to the fluid path layer 1118 using a second fluid path adhesive layer 1120. A valve spacer layer 1124 over a valve membrane layer 1126 can be beneath the valve via layer 1122. A valve seat layer 1128 can be beneath the valve membrane layer 1126 and an etched layer 1130 can be beneath the valve seat layer 1128. In some embodiments, the etched layer 1130 can include cut-outs for forming pneumatic lines and/or ports for controlling the valves. The layers for forming various components of the valves can be bonded to one another using adhesive material layers adjacent to each of the various layers (e.g., pressure sensitive adhesive and/or other suitable types of adhesive material), the adhesive material layers having cut-outs corresponding to the cut-outs of the adjacent layers. In some embodiments, an activated valve can apply pressure upon a corresponding fluid channel above the valve such that the valve pinches off fluid flow in the corresponding fluid channel.

Figure 12A:
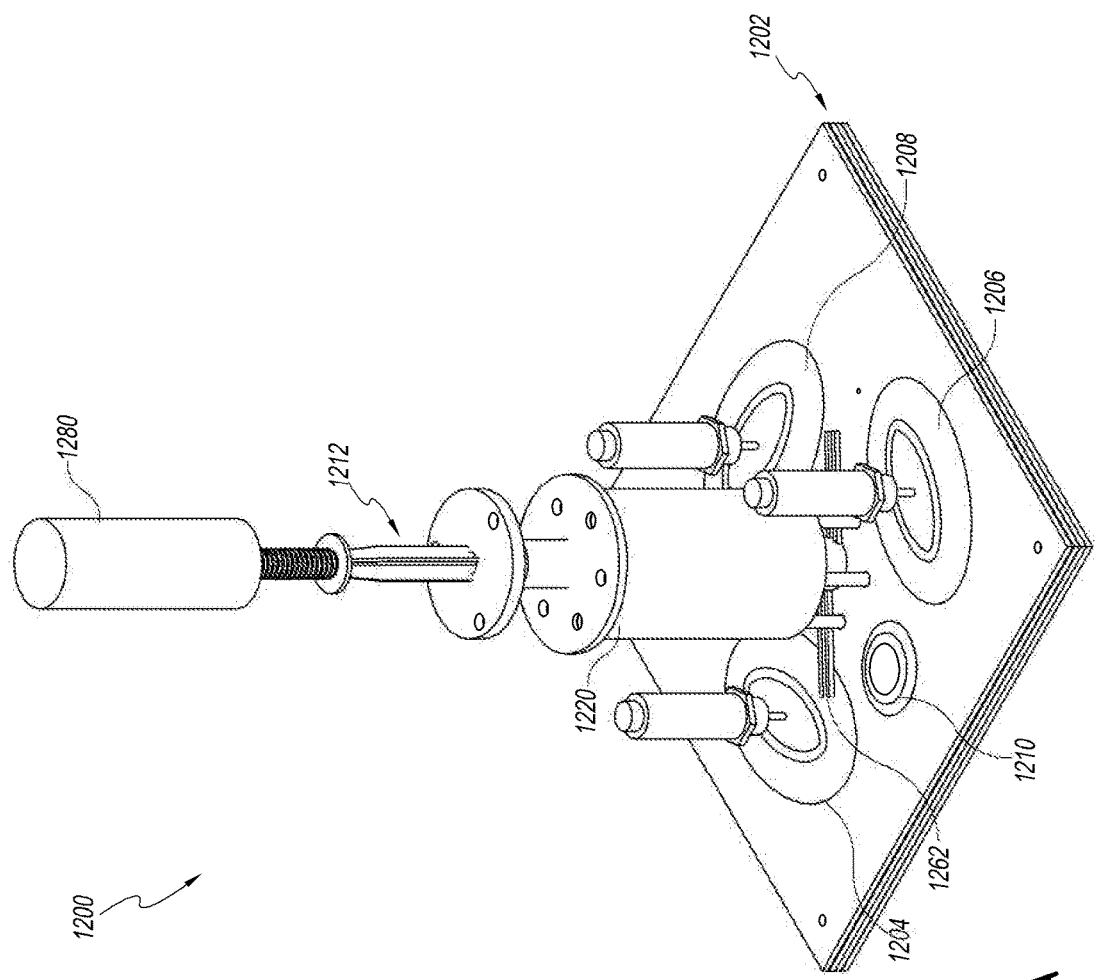
FIGS. 12A through 12C show an example of a purification apparatus which includes a linear actuator coupled to a syringe of the purification apparatus.
Figure 12C:
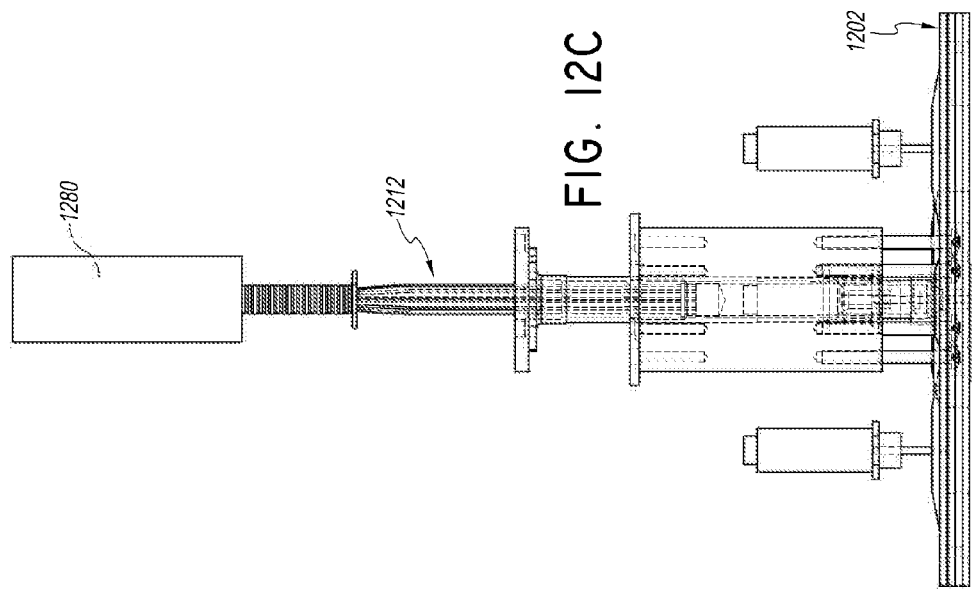
Figure 12B:
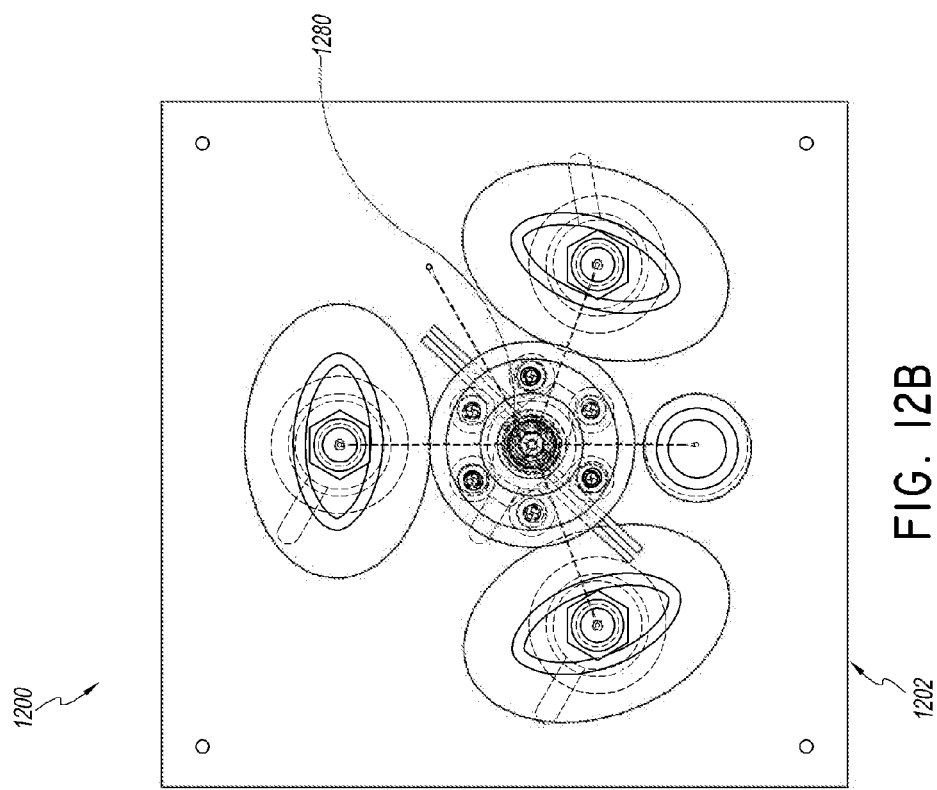

FIGS. 12A through 12C show an example of a purification apparatus 1200 which can include a linear actuator 1280 coupled to a syringe 1212 for controlled metering of a fluid from the syringe 1212 into a disposable cartridge 1202 coupled to the syringe 1212 (e.g., coupled to the syringe 1212 by using a syringe holder 1220). The purification apparatus 1200 can include a first fluid pouch 1204, a second fluid pouch 1206, a third fluid pouch 1206 and/or an elution fluid pouch 1210. In some embodiments, the purification apparatus 1200 can include a heater 1262 for heating a silica based membrane (SBM) containing compartment (e.g., positioned between the syringe 1212 and the disposable cartridge 1202). The syringe 1212 can include a syringe plunger in a syringe barrel, and the linear actuator 1280 can be coupled to the syringe plunger such that movement of the syringe in a proximal and/or distal direction relative to the syringe barrel can be accurately controlled to facilitated application of a controlled negative force and/or positive force upon fluid within the syringe 1212. The purification apparatus 1200 can have a configuration similar to that of the purification apparatus 500 shown in FIGS. 5A through 5C.

In some embodiments, the linear actuator 1280 can be used to facilitate drawing and/or dispensing an accurate amount of fluid, for example as defined by a user. In some embodiments, the linear actuator 1280 can have a resolution of about 20 nanoliters (nL) to about 80 nL, including about 25 nL to about 80 nL, for example for a syringe having a fluid capacity of about 1 milliliters (mL) to about 3 mL. For example, the linear actuator 1280 can have a resolution of about 25 nL for a syringe having a fluid capacity of about 1 mL, and a resolution of about 80 nL for a syringe having a fluid capacity of about 3 mL. In some embodiments, the linear actuator 1280 may be advantageous for controlled metering of fluids in the sub-nanoliter range.

In some embodiments, the linear actuator 1280 facilitates multisampling of different reagents and/or fluids. For example, the linear actuator 1280 can facilitate holding a quantity of a fluid within the syringe 1212 such that the fluid can be infused into a chamber of the disposable cartridge 1202 of the purification apparatus 1200 (e.g., a first fluid pouch 1204, a second fluid pouch 1206 and/or a third fluid pouch 1208), facilitating mixing of controlled quantities of fluids stored in one or more fluid chambers of the disposable cartridge 1202.

FIG. 12B shows a top-down plan view and FIG. 12C shows a side view of the purification apparatus 1200 including the linear actuator 1280. As described herein, the linear actuator 1280 can be coupled to a syringe plunger of the syringe 1212. As shown in FIG. 12C, for example, the linear actuator 1280 can be coupled to a proximal end of the syringe plunger such that a force applied upon the linear actuator 1280 can be controllably transferred to the syringe plunger.

Figure 13B:
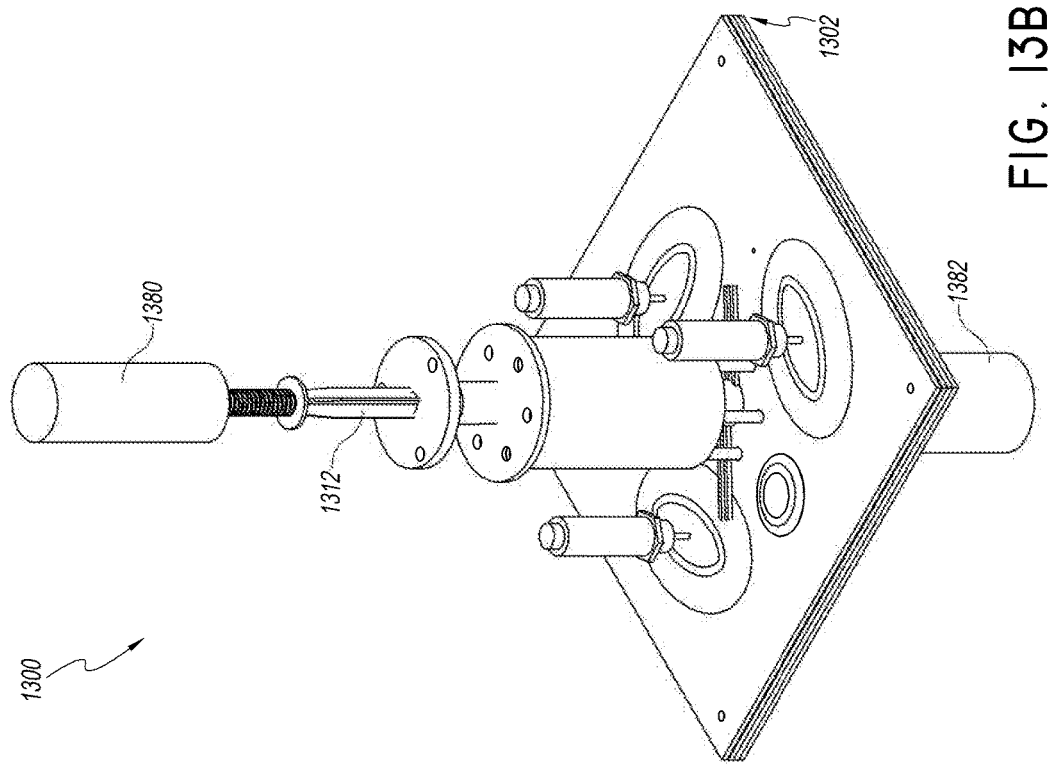
FIGS. 13A and 13B show an example of a purification apparatus which includes a linear actuator coupled to a syringe and a disposable cartridge including a single motorized fluid flow valve.
Figure 13A:
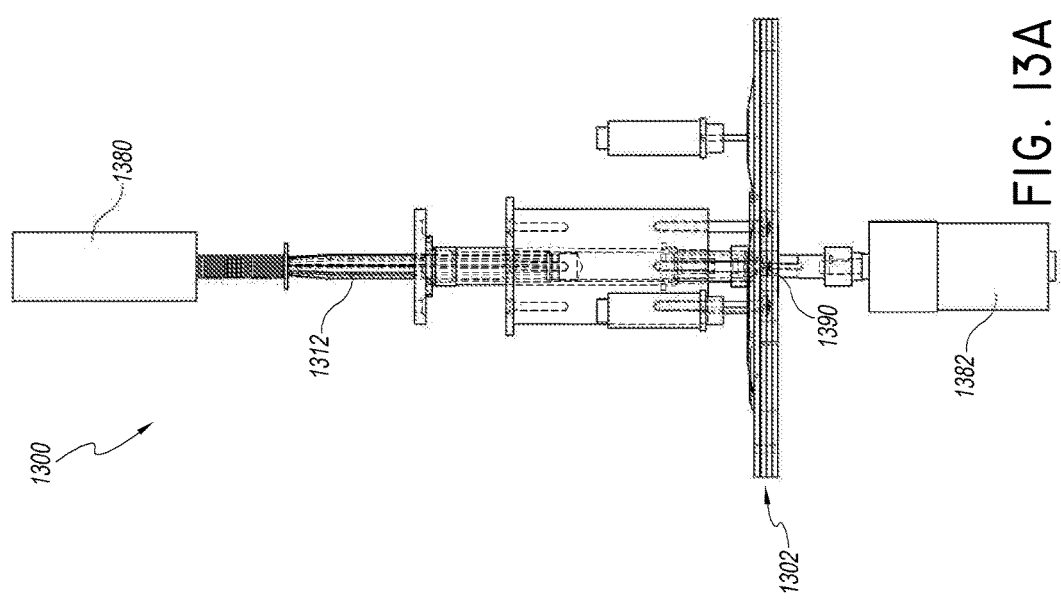

FIGS. 13A and 13B show a purification apparatus 1300 including a disposable cartridge 1302 (e.g., similar to the disposable cartridge 502 as described with reference to FIGS. 5A through 5C), and a linear actuator 1380 (e.g., similar to the linear actuator 1280 as described with reference to FIGS. 12A through 12C) coupled to a syringe 1312. FIG. 13A shows a side view of the purification apparatus 1300 and FIG. 13B shows a perspective view of the purification apparatus 1300. In some embodiments, the purification apparatus 1300 can include a single motorized valve 1390 for valving the fluid channels of the disposable cartridge 1302. In some embodiments, the motorized valve 1390 can be integrated as part of the disposable cartridge 1302. For example, the motorized valve 1390 may provide control of fluid transport into and/or within the disposable cartridge 1302 (e.g., provide control fluid within one or more fluid channels of the disposable cartridge 1302, such as holding fluid within the one or more fluid channels and/or one or more fluid chambers of the disposable cartridge 1302). The single motorized valve 1390 can be used to interrogate different chambers of the disposable cartridge 1302, for example, by rotating the motorized valve 1390 to open and/or close a fluid channel of the different chambers, such as by using a servomotor or a stepper motor 1382. A fluid channel can be opened by the motorized valve 1390 by aligning a valve opening of the motorized valve 1390 with the opening of the fluid channel, and the fluid channel can be closed by the motorized valve 1390 by offsetting (e.g., completely or substantially completely offsetting) the opening of the opening of the fluid channel and the valve opening. In some embodiments, a valve body of the motorized valve 1390 can have an opening for fluid communication with the syringe 1312 (e.g., a distal orifice of the syringe 1312) and/or a silica based membrane (SBM) containing compartment coupled between the syringe 1312 and the disposable cartridge 1302. In some embodiments, a valve body of the motorized valve 1390 can also have one or more openings for indexing different fluid channels of the disposable cartridge 1302, so as to provide fluid communication between the fluid channels and the syringe 1312. For example, the valve body of the motorized valve 1390 can be integrated as a part of the disposable cartridge 1302, and the opening on the valve body for providing fluid communication with the syringe 1312 can be on a plane perpendicular to that of the one or more openings for indexing the fluid channels, such that the valve body can provide fluid communication with the syringe 1312 as it is rotated to index to the different fluid channels of the disposable cartridge 1302. In some embodiments, the valve body of the motorized valve 1390 can include more than one opening for indexing fluid channels within the disposable cartridge 1302, facilitating drawing fluid from more than one fluid chamber at one time (e.g., for mixing the fluids from the different fluid chambers) and/or delivery of fluid to more than one fluid chamber at one time.

Figure 14A:
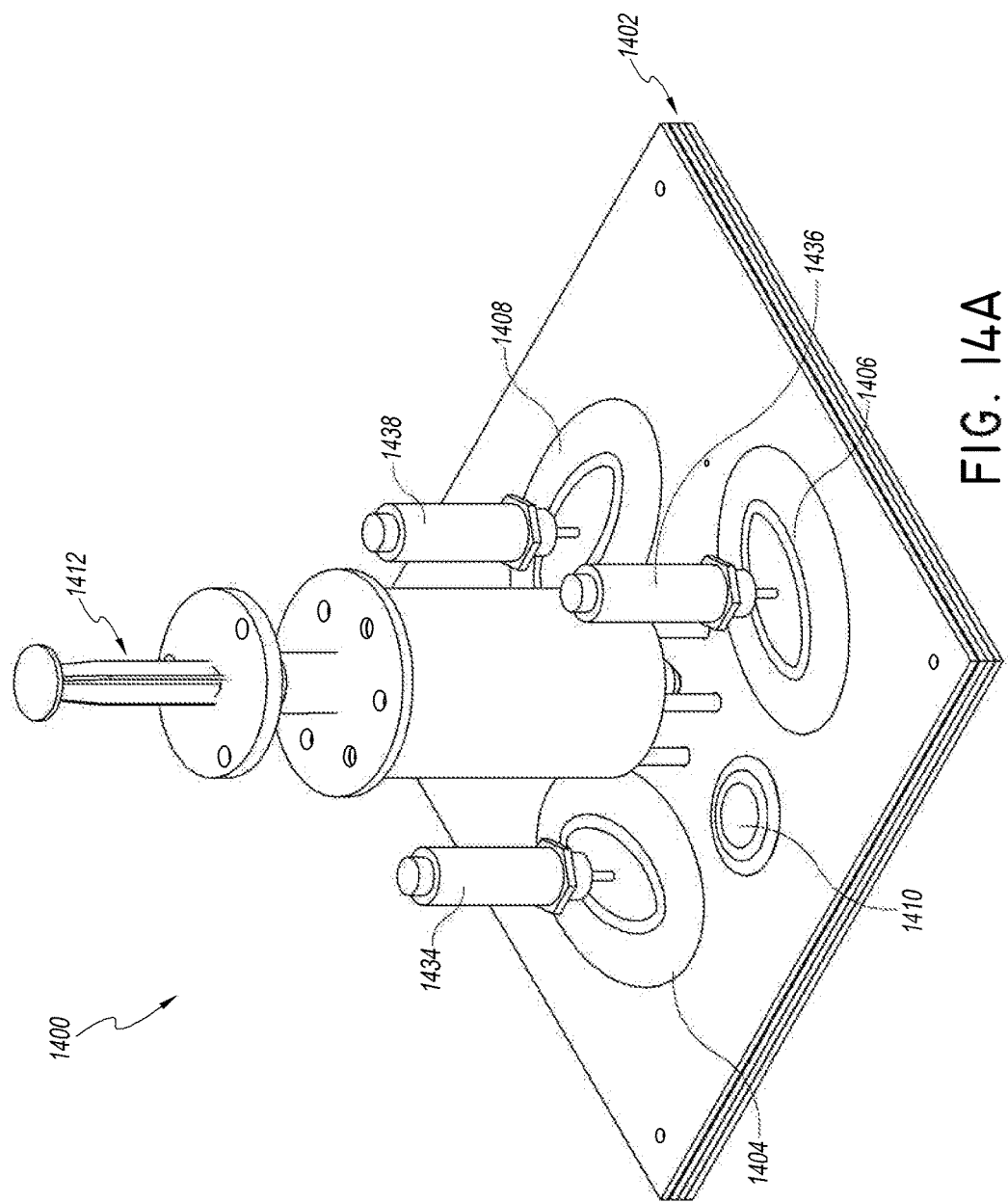

FIGS. 14A through 14C show an example of a purification apparatus 1400. The purification apparatus 1400 can include a disposable cartridge 1402 (e.g., similar to the disposable cartridge 502 as described with reference to FIGS. 5A through 5C) coupled to a syringe 1412. FIG. 14A shows a perspective view of the purification apparatus 1400, FIG. 14B shows a bottom-up plan view of the purification apparatus 1400, and FIG. 14C shows a side view of the syringe 1412 of the purification apparatus 1400 coupled to the disposable cartridge 1402.

In some embodiments, the disposable cartridge 1402 can include a first fluid pouch 1404, a second fluid pouch 1406 and a third fluid pouch 1408, each of which can be punctured by a corresponding actuator, 1434, 1436, 1438, respectively, (e.g., a corresponding electro-mechanical linear actuator) to facilitate control of fluid flow into and/or out from the fluid pouches. In some embodiments, the disposable cartridge 1402 can include one or more valves for controlling fluid flow into and/or out from the fluid pouches. For example, the disposable cartridge 1402 can include a valve for each of the first fluid pouch 1404, the second fluid pouch 1406 and the third fluid pouch 1408, such as valves 1414, 1416, 1418, respectively. In some embodiments, the disposable cartridge 1402 can include a valve 1420 for an elution fluid chamber 1410, for controlling fluid flow into and out from the elution fluid chamber 1410.

In some embodiments, one or more of the valves 1414, 1416, 1418, 1420 can be fabricated using a thin moldable membrane sandwiched within the fluidic network. In some embodiments, one or more of the valves 1414, 1416, 1418, 1420 can be a one-way, two-way or three-way pick-and-place micro valves within the fluidic channels. Activation of a valve can be done with air pressure fed from a pneumatic line (e.g., for pneumatic valves), application of thermal energy (e.g., such using a resistive heater for applying thermal energy to open and/or close thermally responsive valves), and/or by through any other electromechanical means.

Figure 15A:
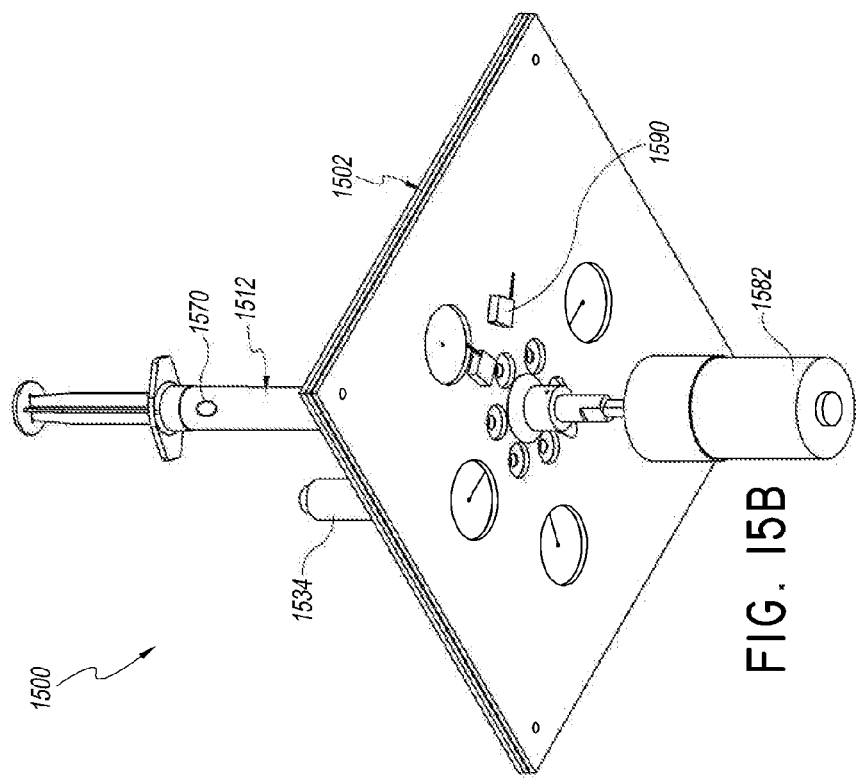
FIGS. 15A and 15B show an example of a purification apparatus which includes a motorized fluid flow valve.
Figure 15B:
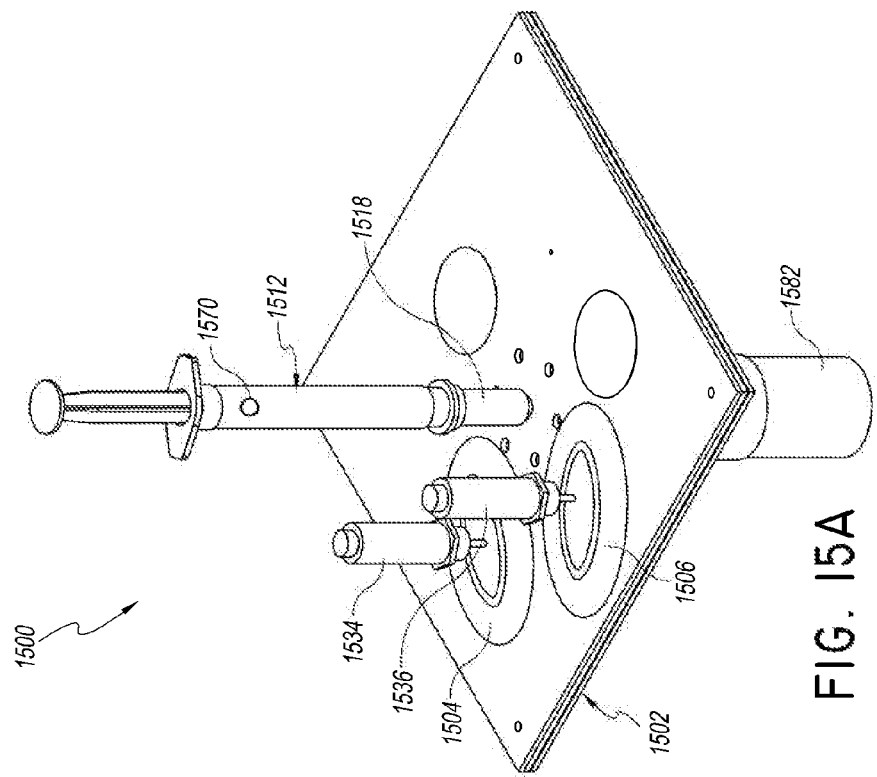

FIGS. 15A and 15B shows an example of a purification apparatus 1500. FIG. 15A shows a top-down perspective view of the purification apparatus 1500 and FIG. 15B shows a bottom-up perspective view of the purification apparatus 1500. The purification apparatus 1500 can include a syringe 1512 and a silica based membrane (SBM) containing compartment 1418 coupled to a disposable cartridge 1502. The syringe 1512 can include an air vent 1570 (e.g., for drawing air into the syringe, for example to pass air over the SBM in the SBM containing compartment 1518, for relieving pressure of the disposable cartridge 1502 when processing an analyte solution, and/or for facilitating escape of volatile byproducts). The disposable cartridge 1502 can include one or more fluid chambers and/or pouches (e.g., fluid pouches 1504, 1506). In some embodiments, the purification apparatus includes an actuator for puncturing one or more of the fluid pouches and/or chambers of the disposable cartridge to facilitate fluid flow into and/or out from the fluid pouches and/or chambers (e.g., actuators 1534, 1536 for puncturing fluid pouches 1504, 1506, respectively).

In some embodiments, the purification apparatus 1500 can include a single motorized valve 1590 for valving the fluid channels of the disposable cartridge 1502. For example, the motorized valve 1590 may provide control of fluid transport into and/or within the disposable cartridge 1502 (e.g., provide control fluid within one or more fluid channels of the disposable cartridge 1502, such as holding fluid within the one or more fluid channels and/or one or more fluid chambers of the disposable cartridge 1502. The single motorized valve 1590 can be used to interrogate different chambers of the disposable cartridge 1302, for example, by rotating the motorized valve 1590 to open and/or close a fluid channel of the different chambers, such as by using a servomotor or a stepper motor 1582. A fluid channel can be opened by the motorized valve 1590 by aligning a valve opening of the motorized valve 1582 with the opening of the fluid channel, and the fluid channel can be closed by the motorized valve 1590 by offsetting (e.g., completely or substantially completely offsetting) the opening of the opening of the fluid channel and the valve opening.

Figure 16:
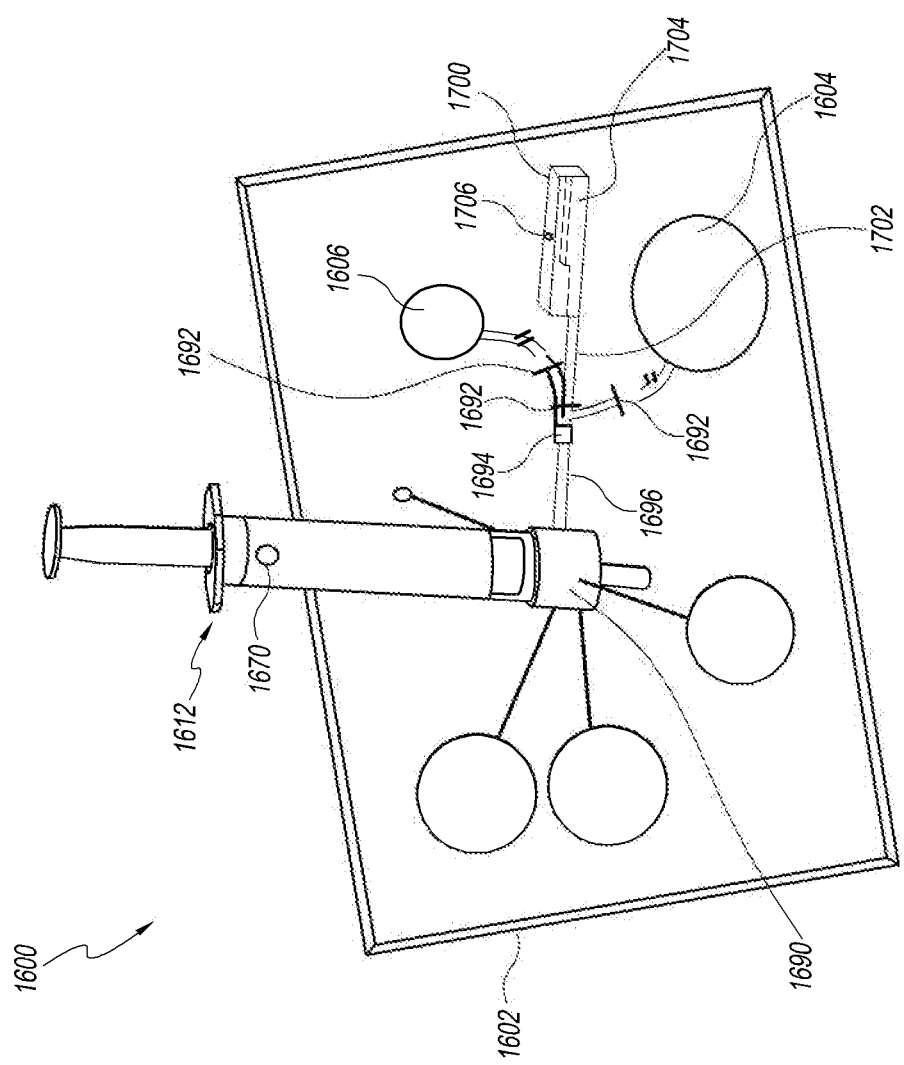
FIG. 16 shows an example of a purification apparatus including a drying chamber.

FIG. 16 shows an example of a purification apparatus 1600 including a single motorized valve 1690 (e.g., a motorized valve proximate to an access port of the disposable cartridge 1602), and one or more additional valves 1692 (e.g., micro valves) at a location more proximal to one or chambers of the disposable cartridge 1602 for controlling fluid flow into and/or out from the respective chambers. Referring to FIG. 16, the purification apparatus 1600 can include a syringe 1612 coupled to the disposable cartridge 1602, the syringe 1612 including an air vent 1670 along a sidewall of a syringe barrel. In some embodiments, a silica based membrane (SBM) 1694 can be placed in a channel 1696 (e.g., the SBM can be embedded in and/or integrated as a part of the channel 1696) within the disposable cartridge 1602, where the channel 1696 can be in fluid communication with an orifice at a distal end of the syringe 1612. In some embodiments, the disposable cartridge 1602 can include a waste fluid chamber 1604, an elution fluid chamber 1606, and a drying chamber 1700. For example, the waste fluid chamber 1604 can be configured to provide common storage for waste fluid for the disposable cartridge 1602, for example providing storage for fluid which has been previously contacted with the SBM 1394 of the disposable cartridge 1602 (e.g., fluid which has been contacted with the SBM is not sent back to the chamber from which the fluid was withdrawn but instead can be stored in waste fluid chamber 1604). In some embodiments, the channel 1696 can be in fluid communication with fluid channels leading to the waste fluid chamber 1604, the elution fluid chamber 1606, and/or the drying chamber 1700. In some embodiments, the disposable cartridge 1602 includes a wicking material 1702 along a channel leading to the drying chamber 1700, and an absorbent pad 1704 in the drying chamber, for example to facilitate drying of the SBM. In some embodiments, the drying chamber 1700 can include an air vent 1706 for facilitating entry and exit of air from the drying chamber 1700, such as during drying of the SBM 1694.

A micro valve 1692 may be located proximate to each of the waste fluid chamber 1604, the elution fluid chamber 1606 and/or the drying chamber 1700. For example, the micro valve 1692 controlling fluid flow through the channel leading to the elution fluid chamber 1606 and the micro valve 1692 controlling fluid flow through the channel leading to the drying chamber 1700 can remain closed when an analyte solution (e.g., a sample solution including nucleic acid to be purified) is passed over the SBM 1694 such that the analyte (e.g., nucleic acid of interest) can selectively bind to the SBM, and/or while the SBM 1694 is washed to remove one or more contaminants.

In some embodiments, the SBM 1694 is dried prior to elution of the analyte which has been selectively bound to the SBM 1694. For example, the micro valve 1692 controlling fluid flow from the elution fluid chamber 1606 and the micro valve 1692 controlling fluid flow to the waste fluid chamber 1604 can be closed for drying of the SBM 1692, while the micro valve 1692 for controlling fluid flow into the drying chamber 1700 can be opened. The air vent 1706 on the drying chamber 1700 can be used to expel volatile agents from the disposable cartridge 1602, drawing air into the disposable cartridge 1602 for drying the SBM 1692, and/or can be configured to provide pressure relief for the disposable cartridge 1602. For example, air can be drawn into the drying chamber 1700 through the air vent 1706 if a negative pressure is applied using the syringe 1612. In some embodiments, air can be expelled through the air vent 1706 for drying the SBM 1694 when a positive force is applied using the syringe 1612, including for example subsequent to a process in which air was drawn into the disposable cartridge 1602 through the air vent 1706 of the drying chamber 1700 and/or the syringe air vent 1670.

In some embodiments, during the elution of analyte from the SBM 1694, the micro valve 1692 controlling fluid flow from the elution fluid chamber can be opened while the micro valve 1692 controlling fluid flow to the waste fluid chamber 1604 is closed. In some embodiments, the waste fluid chamber 1604 can be in fluid communication with the drying chamber 1700, for example to reduce, prevent or substantially backflow of waste fluid due to any pressure differential during the operation of the valves of the disposable cartridge 1602.

Figure 17A:
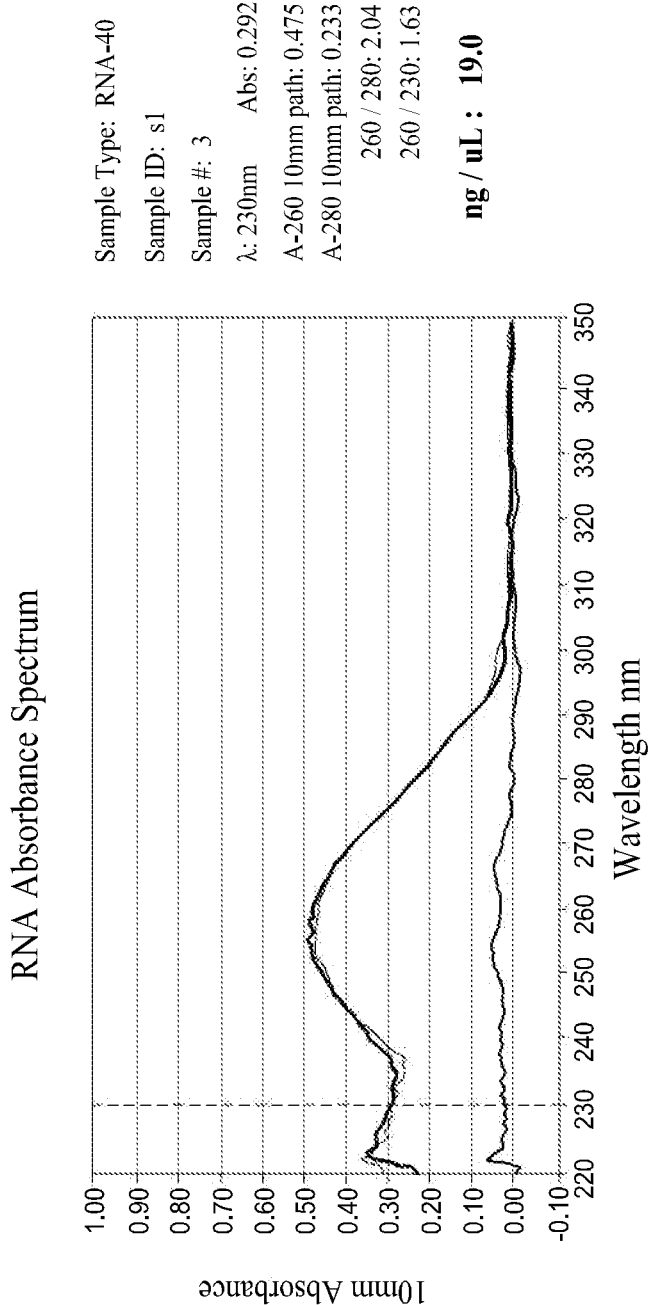
FIG. 17A is an absorption spectrum of a sample of nucleic acid.

FIG. 17A shows an example of an absorption spectrum of a nucleic acid sample, such as for determining a purity of the nucleic acid sample. For example, FIG. 17A shows an ultra-violate (UV) absorbance spectrum of a sample of ribonucleic acid (RNA), at various wavelengths shown in nanometers (nm), such as within a spectrum of about 220 nanometers (nm) to about 350 nm. The purity of captured nucleic acid from the silica based membrane can be determined using the UV absorption spectroscopy information shown in FIG. 17A. The concentration of nucleic acid can be determined using the Beer-Lambert law, which predicts a linear change in absorbance with concentration. An A260 reading of 1.0 is equivalent to about 40 microgram/milliliter (μg/mL) of RNA. The Optical Density at 260 nm can be used to determine the RNA concentration in a solution. RNA has its absorption maximum at 260 nm and the ratio of the absorbance at 260 nm and 280 nm can be used to assess the RNA purity of an RNA preparation. Pure RNA has an A260/A280 of 2.1. FIG. 17A shows that the RNA obtained from the present system obtained purity with an A260/A280 of 2.04.

Figure 17B:
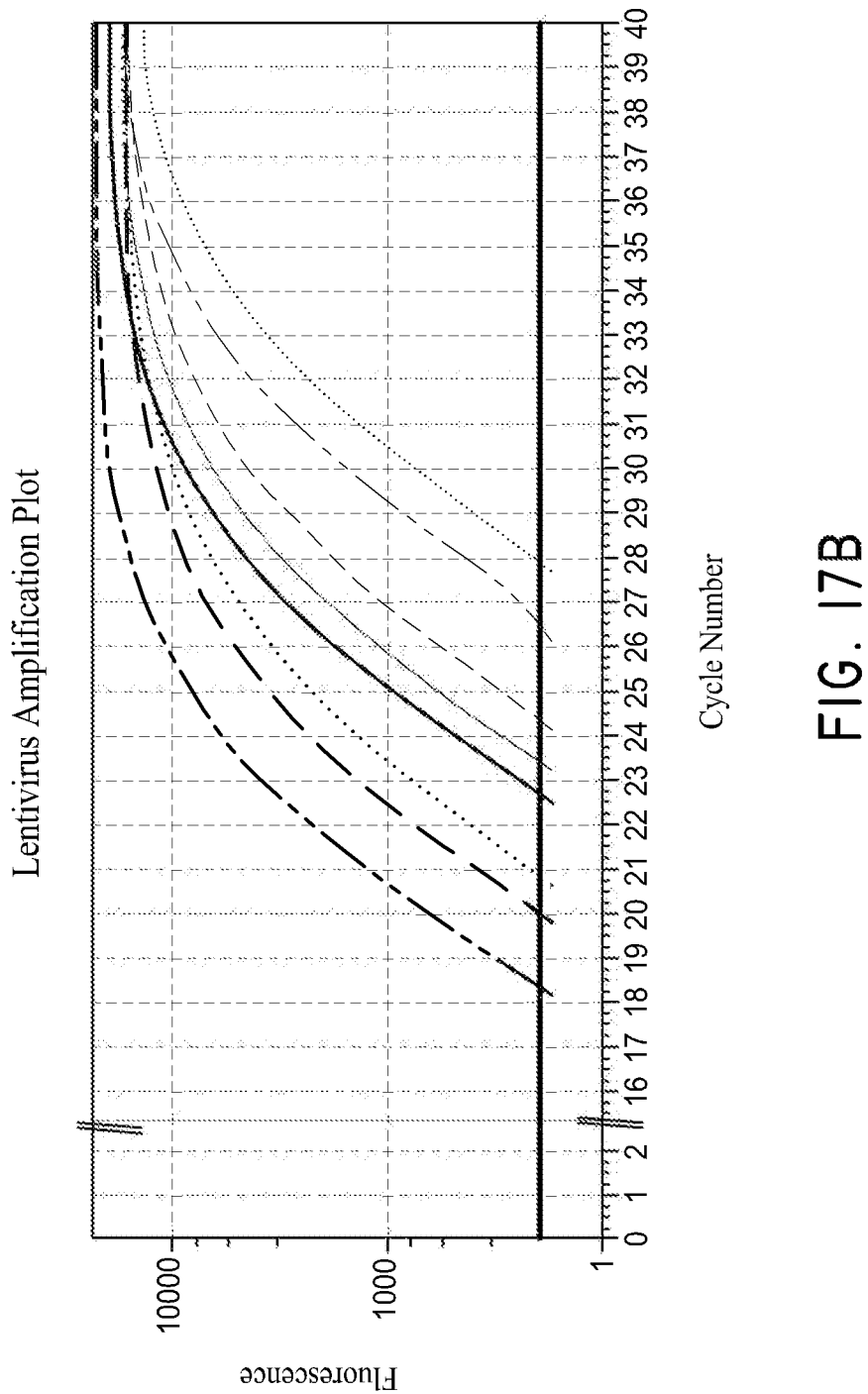
FIG. 17B is an amplification graph for a concentration determination.

FIG. 17B shows an amplification plot for determining a concentration of target nucleic acid a sample. Nucleic acid concentration can be assessed using different methods, such as absorbance (e.g., using a measure of optical density) and fluorescent DNA-binding dyes (e.g., SYBR® Green Master Mixes available from Life Technologies, Corp., of Grand Island, N.Y.). In some embodiments, other methods to determine concentration can also be suitable, such as agarose gel electrophoresis and/or luciferase-pyrophosphorylation-coupled quantitation systems. The amplification plot of FIG. 17B shows a spiked in viral copies of lentivirus in whole blood processed from the disposable device compared to the standard benchtop.

Figure 17C:
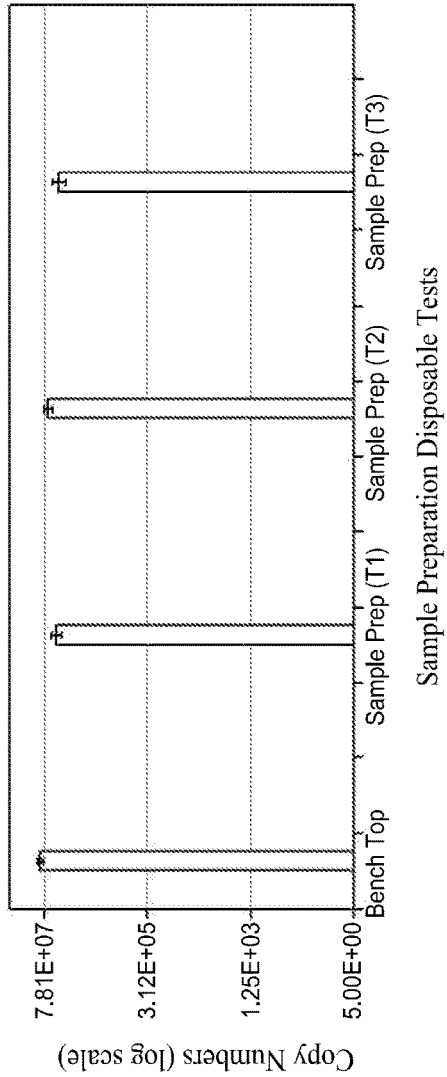
FIG. 17C is a bar graph of the number of viral copies of the lentivirus.

FIG. 17C is a bar graph of the number of viral copies of lentivirus in mouse whole blood. The bar graph of 17C shows a spike in the number of viral copies of the lentivirus, as compared to the standard benchtop.

Figure 17D:
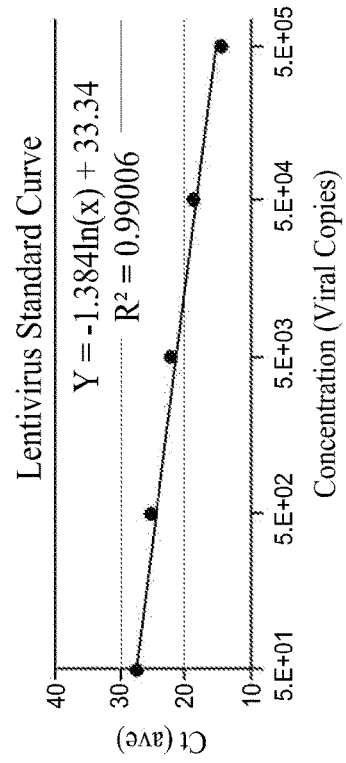
FIG. 17D is a standard curve used for quantification of a number of viral copies of lentivirus.

FIG. 17D is a standard curve used in quantifying the number of viral copies from lentivirus RNA purified from the disposable device and the benchtop purification process.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

The headings provided herein, if any, are for convenience only and do not necessarily affect the scope or meaning of the devices and methods disclosed herein.

What is claimed is:

1. A nucleic acid purification kit comprising:
    a disposable cartridge having a layered configuration, the disposable cartridge comprising a first surface of a first layer of the disposable cartridge and an access port on the first surface, and each of a plurality of layers of the disposable cartridge being joined to an adjacent layer by a corresponding adhesive material layer;
    a first fluid pouch and a second fluid pouch coupled to the first surface of the disposable cartridge, wherein the first fluid pouch comprises a first air vent configured to be opened for releasing a stored first reagent from the first fluid pouch into the disposable cartridge and the second fluid pouch comprises a second air vent configured to be opened for releasing a stored second reagent from the second fluid pouch into the disposable cartridge; and
    a disposable silica-containing compartment for capturing the nucleic acid, wherein the disposable silica-containing compartment has a distal opening and a proximal opening, the distal opening of the disposable silica-containing compartment being configured to couple to the access port on the first surface of the disposable cartridge, the silica-containing compartment being operably connected to the disposable cartridge, the proximal opening configured to be coupled to a device configured to perform one or more of: delivering fluid into the disposable cartridge and withdrawing fluid out of the disposable cartridge;
    wherein the disposable cartridge comprises a first layer comprising a first cut-out portion for forming a first fluid chamber in fluid communication with the first fluid pouch, the first fluid pouch and the first fluid chamber being in fluid communication with the access port and being configured for receiving and storing a discrete quantity of the first reagent, wherein the first reagent is subsequently released from the first fluid pouch and the first fluid chamber to contact silica of the disposable silica-containing compartment, wherein the disposable cartridge comprises a second layer comprising a second cut-out portion for forming a second fluid chamber in fluid communication with the second fluid pouch, the second fluid pouch and the second fluid chamber being in fluid communication with the access port and being configured for receiving and storing a discrete quantity of the second reagent, wherein the second reagent is subsequently released from the second fluid pouch and the second fluid chamber to contact silica of the disposable silica-containing compartment, wherein the disposable cartridge comprises at least one additional layer comprising a fluid channel cut-out portion for forming a fluid channel to fluidly connect at least one of the first fluid chamber and the second fluid chamber to the access port on the first surface of the disposable cartridge, and wherein each of the first layer, the second layer and the at least one additional layer comprises on a surface the corresponding adhesive material layer, the corresponding adhesive material layer comprising a respective cut-out portion corresponding to the first fluid chamber, the second fluid chamber or the fluid channel.

2. The purification kit of claim 1, further comprising a disposable syringe for coupling to the proximal opening of the disposable silica-containing compartment, the disposable syringe being configured to deliver a fluid to or withdraw the fluid from the disposable cartridge.

3. The purification kit of claim 2, wherein the disposable syringe comprises a syringe barrel having an air vent on a sidewall of the syringe barrel, the air vent being configured for drawing air into the syringe.

4. The purification kit of claim 1, wherein the first fluid chamber comprises an elution fluid chamber configured to retain a fluid for eluting the nucleic acid from the silica-containing compartment.

5. The purification kit of claim 1, wherein the disposable cartridge is valveless.

6. The purification kit of claim 1, wherein the disposable cartridge comprises a valve for controlling fluid transport between the access port and at least one of the first fluid chamber and the second fluid chamber.

7. The purification kit of claim 1, wherein the silica-containing compartment comprises a portion of a sidewall heated by a heater.

8. The purification kit of claim 1, wherein the disposable cartridge further comprises a plurality of mounting holes on the first surface for coupling with a corresponding plurality of syringe assembly mounting fixtures, the plurality of mounting holes at equal distances from one another surrounding the access port.

9. The purification kit of claim 1, further comprising a fourth layer comprising a fourth cut-out portion for forming a fourth fluid chamber for receiving a fourth reagent.

10. The purification kit of claim 1, further comprising a third layer comprising a third cut-out portion for forming a third fluid chamber for receiving a third reagent.

11. The purification kit of claim 10, further comprising a third fluid pouch coupled to the first surface of the disposable cartridge, the third fluid pouch being in fluid communication with the third fluid chamber, the third fluid pouch and the third fluid chamber being configured for receiving and storing a discrete quantity of the third reagent, wherein the third reagent is subsequently released from the third fluid pouch and the third fluid chamber to contact silica of the disposable silica-containing compartment.

12. The purification kit of claim 1, wherein the second layer further comprises a cut-out portion for forming the first fluid chamber and the first layer further comprises a cut-out portion for forming the second fluid chamber.

13. The purification kit of claim 1, wherein each of the first layer, the second layer and the additional layer further comprises cut-out portions for forming a plurality of mounting holes for coupling with a corresponding plurality of syringe assembly mounting fixtures.

14. An apparatus for purifying nucleic acid, the apparatus comprising:
  a disposable cartridge having a layered configuration, the disposable cartridge comprising a first surface of a first layer of the disposal cartridge and an access port on the first surface, each of a plurality of layers of the disposable cartridge being joined to an adjacent layer by a corresponding adhesive material layer, and the disposable cartridge including an embedded silica-containing material for capturing the nucleic acid;
  a first fluid pouch and a second fluid pouch coupled to the first surface of the disposable cartridge, wherein the first fluid pouch comprises a first air vent configured to be opened for releasing a stored first reagent from the first fluid pouch into the disposable cartridge and the second fluid pouch comprises a second air vent configured to be opened for releasing a stored second reagent from the second fluid pouch into the disposable cartridge;
  a disposable syringe for coupling to the access port on the first surface of the disposable cartridge, wherein the disposable syringe is configured to deliver a fluid to or withdraw the fluid from the disposable cartridge such that the silica-containing material is contacted with the fluid,
  wherein the disposable cartridge comprises a first layer comprising a first cut-out portion for forming a first fluid chamber in fluid communication with the first fluid pouch, the first fluid pouch and the first fluid chamber being in fluid communication with the access port and being configured for receiving and storing a discrete quantity of the first reagent, wherein the first reagent is subsequently released from the first fluid pouch and the first fluid chamber to contact silica of the embedded silica-containing material,
  wherein the disposable cartridge comprises a second layer comprising a second cut-out portion for forming a second fluid chamber in fluid communication with the second fluid pouch, the second fluid pouch and the second fluid chamber being in fluid communication with the access port and being configured for receiving and storing a discrete quantity of the second reagent, wherein the second reagent is subsequently released from the second fluid pouch and the second fluid chamber to contact silica of the embedded silica-containing material,
  wherein the disposable cartridge further comprises at least one additional layer comprising a first fluid channel cut-out portion for forming a first fluid channel to fluidly connect at least one of the first fluid chamber and the second fluid chamber with the access port on the first surface of the disposable cartridge, and wherein each of the first layer, the second layer and the at least one additional layer comprises on a surface a corresponding adhesive material layer, the corresponding adhesive material layer comprising a respective cut-out portion corresponding to the first fluid chamber, the second fluid chamber or the fluid channel.

15. The apparatus of claim 14,
wherein the disposable cartridge further comprises at least one additional layer comprising a second fluid channel cut-out portion for forming a second fluid channel to fluidly connect at least the other one of the first fluid chamber and the second fluid chamber with the access port on the first surface of the disposable cartridge, and
wherein the silica-containing material is embedded in a sidewall of the second fluid channel within the disposable cartridge.

16. The apparatus of claim 15, wherein the disposable cartridge further comprises at least one additional layer comprising a drying chamber cut-out portion for forming a drying chamber in fluid connection with the second fluid channel.

17. The apparatus of claim 16, wherein the first fluid chamber comprises an elution fluid chamber and the second fluid chamber comprises a waste fluid chamber in fluid communication with the access port.

18. The apparatus of claim 17, further comprising a first valve for controlling fluid flow to the elution fluid chamber, a second valve for controlling fluid flow to the waste fluid chamber, and a third valve for controlling fluid flow to the drying chamber.

19. The apparatus of claim 16, wherein a sidewall of the drying chamber comprises an air vent.

20. The apparatus of claim 16, wherein the second fluid channel between the embedded silica-containing material and the drying chamber further comprises a wicking material.

21. The apparatus of claim 16, wherein the drying chamber further comprises an adsorbent material for drying the silica-containing material.

* * * * *